United States Patent [19]

Bisagni et al.

[11] 4,266,060
[45] May 5, 1981

[54] DIPYRIDO [4,3-b] [3,4/f] INDOLES AND PROCESS FOR OBTAINING THEM

[75] Inventors: Emile Bisagni, Orsay; Claire Ducrocq, Les Ulis; Christian Rivalle, Villebon; Pierre Tambourin, Orsay les Ulis; Francoise Wendling, Paris; Jean-Claude Chermann, Elancourt; Luc Montagnier, Le Plessis-Robinson, all of France

[73] Assignee: Agence Nationale de Valorisation de la Recherche (ANVAR), Neuilly sur Seine, France

[21] Appl. No.: 896,101

[22] Filed: Apr. 13, 1978

[30] Foreign Application Priority Data

Apr. 13, 1977 [FR] France ............................... 77 11148

[51] Int. Cl.³ ................. C07D 471/14; A61K 31/47
[52] U.S. Cl. ................................. 546/64; 260/465 D; 546/117; 546/141; 546/143; 562/434; 562/438; 562/442; 562/433; 424/258; 568/424
[58] Field of Search ........................... 546/64; 424/258

[56] References Cited

U.S. PATENT DOCUMENTS 3,933,827  1/1976  Brossi et al. ........................... 546/70
4,045,565  8/1977  Le Pecq et al. ..................... 546/70 X

OTHER PUBLICATIONS

Chermann, et al, C. R. Hebd. Seances Acad. Sci., Ser. D 1977, 285(8), 945–948 (Abstract only supplied).
Hayat, et al., Chemical Abstracts, vol. 83, 542s (1975).
Nguyen Dat Xuong, et al., Chemical Abstracts, vol. 84, 90379s (1976).
Rastogi, et al., Chemical Abstracts, vol. 78, 29651j (1973).

Primary Examiner—Donald G. Daus
Assistant Examiner—Diana G. Rivers
Attorney, Agent, or Firm—Sprung, Felfe, Horn, Lynch & Kramer

[57] ABSTRACT

The invention relates to compounds of formula:

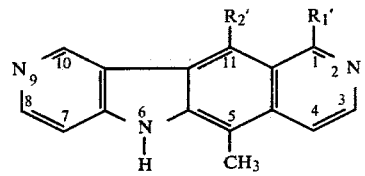

wherein
R'$_1$=H, OH or an alkyl group, preferably a lower alkyl group, alkylthio or alkoxy, an halogen or an amino group,
R'$_2$=H or a lower alkyl group.

These compounds have antitumoral and antiviral properties useful for the treatment of cancers.

16 Claims, No Drawings

DIPYRIDO [4,3-B] [3,4-f] INDOLES AND PROCESS FOR OBTAINING THEM

The present invention, in which participated Mr. Emile BISAGNI, Miss Claire DUCROCQ, Mr. Christian RIVALLE, Mr. Pierre TAMBOURIN and Miss Francçise WENDLING of the "Fondation CURIE—Institut du Radium"—as well as MM. Jean-Claude CHERMANN and Luc MONTAGNIER of the "INSTITUT PASTEUR", relates to dipyrido [4,3-b][3,4-f] indoles and a process for obtaining thereof. The invention also relates to pharmaceutical compositions containing the dipyrido [4,3b][3,4-f] indoles and the therapeutic applications thereof.

It is known that 9-methoxy-ellipticine, its O-demethylated derivative and, especially, 2-N-methyl-9-hydroxy-ellipticinium acetate, have therapeutic properties which are interesting in the field of cancerology; these compounds are pyrido [4,3b] carbazoles of general formula $I_a$ and $I_b$

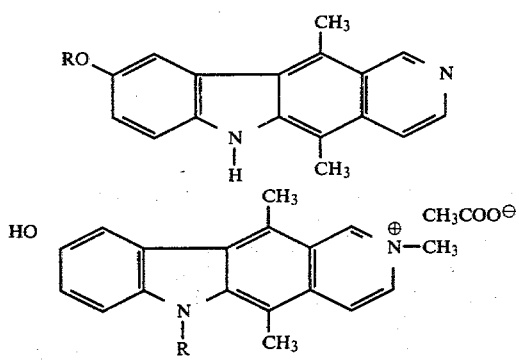

in which R represents $CH_3$ or H.

To this end, reference may be made to the following articles:
J. B. LE PECQ, C. GOSSE, NGUYEN DAT XUONG, S. CROS and C. PAOLETTI: Cancer Research 36 p 3067–3076 (1976) and
J. B. LE PECQ, C. GOSSE, NGUYEN DAT XUONG, and C. PAOLETTI: C. R. Acad. Sci. Paris Série D 281 p 1365 (1975).

Novel compounds, dipyrido [4,3-b][3,4-f] indoles, have now been found, which also have therapeutic properties which are interesting in the field of cancerology.

The dipyrido [4,3-b][3,4-f] indoles according to the present invention correspond to formula II:

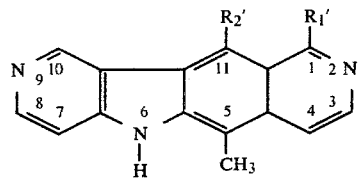

in which: $R'_1$ is hydrogen, hydroxy group, an alkyl group, preferably a lower alkyl group, an alkylthio or alkoxy group, a halogen, such as chloro, or an amino group; $R'_2$ is hydrogen or a lower alkyl group, preferably a methyl group.

In the present specification, the term "lower alkyl" denotes those alkyl groups having from 1 to 3 carbon atoms, and preferably the methyl group.

By way of suitable amino groups, mention may be made of the following group of formula:

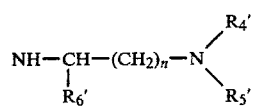

in which n is between 1 and 4, preferably between 1 and 3, $R'_6$ is hydrogen of a lower alkyl group, for example $CH_3$ group and $R'_4$ and $R'_5$ are identical or different and each represent an atom of hydrogen or a lower alkyl group; groups $R'_4$ $R'_5$ are preferably identical and are hydrogen, the methyl group or the ethyl group.

The invention also relates to the pharmaceutically acceptable salts of the dipyrido-indoles of formula (II) as well as their isomeric and tautomeric forms when they exist.

The present invention also relates to a process for obtaining said dipyrido [4,3b][3,4f] indoles.

The process according to the present invention comprises the following steps of:
(1) reacting a 6-amino-isoquinoline with 3-nitro-4-chloro-pyridine to form the corresponding 6-[4'(3'-nitropyridyl)amino]isoquinoline;
(2) hydrogenating said isoquinoline thus obtained into the corresponding amino compound;
(3) reacting the corresponding amino compound with sodium nitrite to form the corresponding triazolopyridine;
(4) converting the triazolopyridine thus obtained into the corresponding dipyrido [4,3-b][3,4f] indole,
(5) possibly forming the pharmaceutically acceptable salt of the dipyrido-indole thus obtained.

The process of the invention may be represented by the following reaction schema:

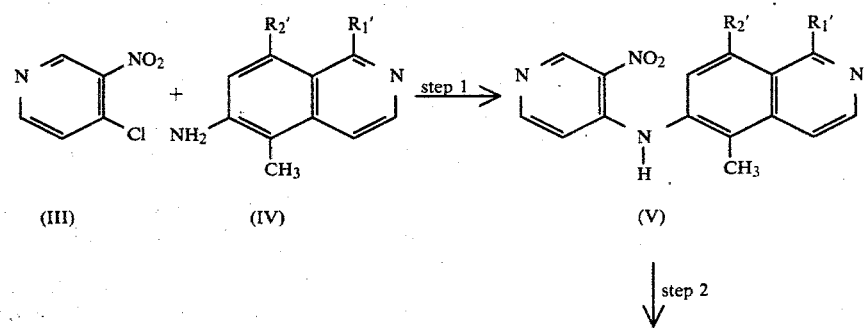

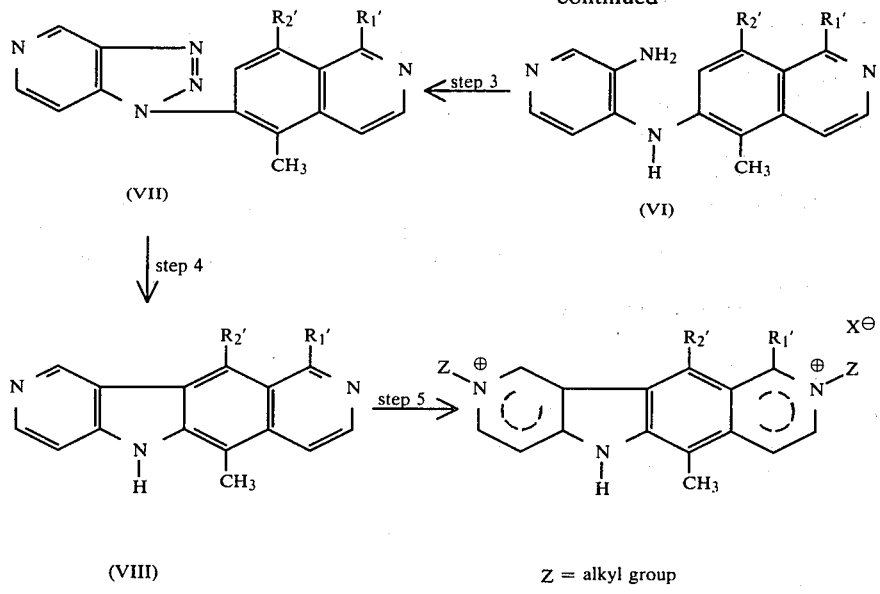

(VII)                      (VI)

(VIII)           Z = alkyl group (IX)

The starting materials used in the process of the invention are therefore the 3-nitro-4-chloro-pyridine of formula (III) and the 6-amino-isoquinolines of formula (IV).

Step 1: of the process of the invention consists in condensing the 3-nitro-4-chloro-pyride of formula III with a 6-amino-isoquinoline of formula IV. This condensation may be effected according to different processes well known to the man skilled in the art, these processes varying according to the nature of the substituents $R'_1$ $R'_2$ of the 6-amino-isoquinoline used in this step.

Thus, when the starting 6-amino-isoquinoline comprises no hydroxy groups, step 1 may be effected in the following manner:

The 6-amino-isoquinoline is dissolved in a suitable inert solvent, such as 1,2-dimethoxy-ethane, a solution of dry acid, sucy as hydrochloric acid, in a dry solvent, is added, then the 3-nitro-4-chloro-pyridine is added. The thus obtained reaction mixture is maintained at reflux until one of the reagents has substantially completely disappeared, this being determined by thin layer chromatography measurement; the solvent is then evaporated.

When the starting 6-amino isoquinoline comprises a hydroxy group, it is advantageous to operate at ambient temperature; the starting materials may be dissolved in an inert solvent, such as for example dimethyflormamide. The reaction mixture obtained by mixture of the solutions of the two starting materials are left at ambient temperature until disappearance of the starting materials which are visible in thin layer chromatography on silica gel. The precipitate formed is then recovered by conventional techniques.

Equimolar or substantially equimolar quantities of the two starting materials are advantageously used.

Step 2 of the process according to the invention consists in a hydrogenation of the 6-[4'-(3'-nitropyridyl-)amino]isoquinoline obtained according to step 1 described hereinabove. This hydrogenation is effected in the presence of a hydrogenation catalyst, such as palladium charcoal. The 6-[4'-(3'-nitropyridyl-)amino]isoquinoline is dissolved in an organic solvent, such as for example acetic acid; a suitable quantity of palladium charcoal is added to this solution and the mixture is stirred in a hydrogen atmosphere until the theoretical absorption of hydrogen. The catalyst is then eliminated by filtration; the solvent is evaporated and the residue obtained is recrystallised from an organic solvent, such as methanol, ethanol, acetonitrile, xylene, etc.

According to step 3) of the process of the invention, the corresponding triazolopyridine is obtained by treating the 6-[4'-(3'-amino-phridyl)amino]isoquinoline of formula VI with sodium nitrite. It is advantageously to carry out this step as follows: the 6-[4'-3'-amino-pyridyl amino]isoquinoline is dissolved in an orgainc acid, such as acetic acid, the mixture obtained is cooled to about 0° C. and an aqueous solution of sodium nitrite in the minimum of water is progressively added. The reaction mixture is stirred until the temperature returns to ambient; the precipitate formed is then washed and dried according to conventional methods.

According to step 4) of the process of the invention, the triazolopyridine obtained according to step 3) is converted into the corresponding dipyrido [4,3-b][3,4-f] indole. In the course of this conversion, an opening of the triazolo ring and a cyclisation are produced to form a dipyrido-indole of formula VIII. This step is carried out in an inert agent, such as paraffin or phenanthrene, having a fairly high boiling point to allow the conversion indicated which occured thermally.

This step is usually carried out at a temperature of 320°–350° C.

Examples for carrying out this step will be given hereinafter.

The dipyrido [4,3-b][3,4-f] idole thus obtained is then possibly converted into a pharmaceutically acceptable salt.

To form these pharmaceutically acceptable salts. it is important to use the suitable agents well known to the man skilled in the art, such as hydrochloric, hydrobromic, succinic, lactic, acetic, phosphoric acids and all other acids commonly used for forming such salts.

The reaction schemas of the preferred proceedings for carrying out the process according to the invention will be indicated hereafter:

PROCEEDING n°1:

This proceeding relates to the obtaining of dipyridoindoles of formula II hereinabove in which $R'_1$ is hydrogen and $R'_2$ is an alkyl group, for example the methyl group; this proceeding is represented by the following diagram for the compound of formula II in which $R'_2$ is a methyl group:

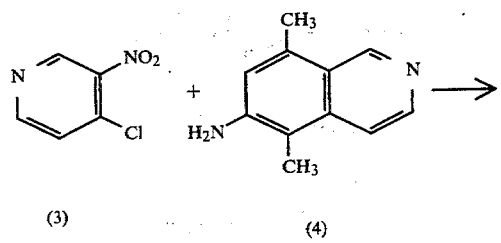

This proceeding will be illustrated by Examples 1 to 4 hereinafter.

PROCEEDING n°2

This proceeding relates to the obtaining of dipyridoindoles of formula II hereinabove in which $R'_1$ is the hydroxy group and $R'_2$ is hydrogen or a lower alkyl group.

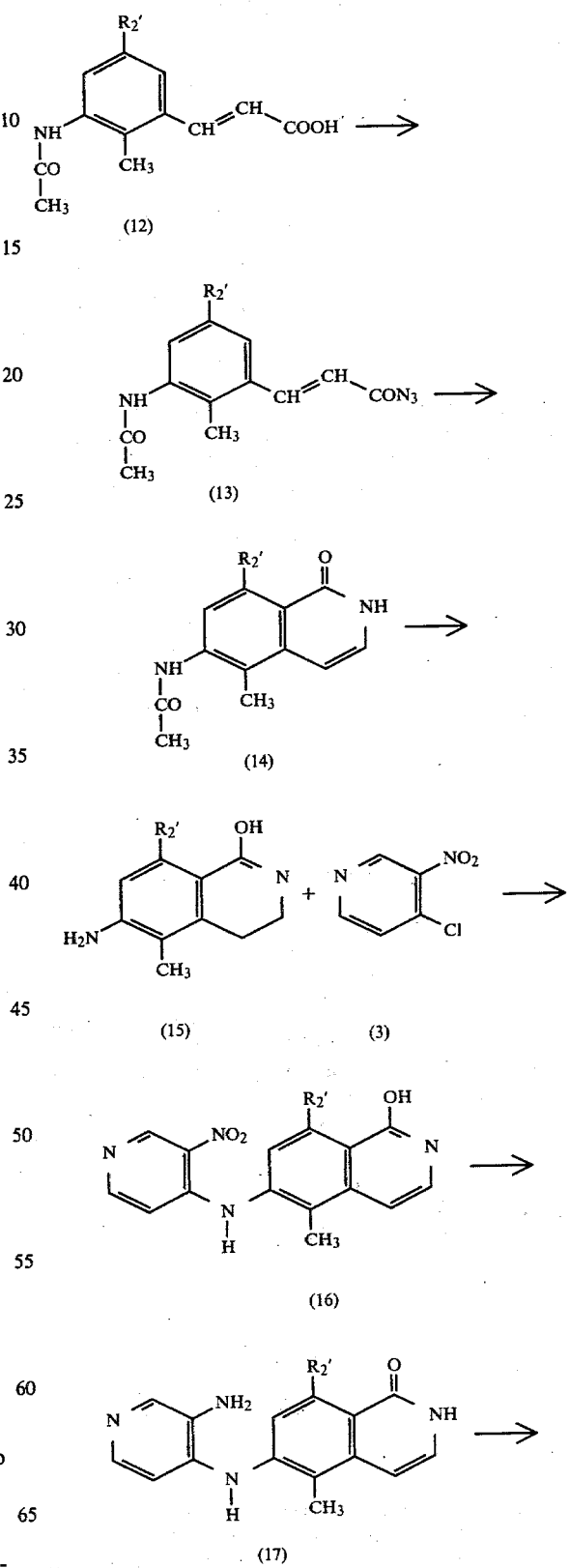

-continued

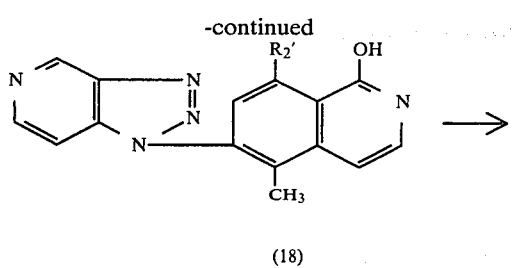

(18)

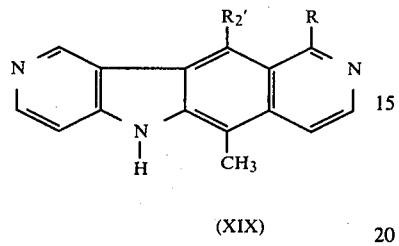

(XIX)

The compounds 19 to 26 described hereinafter in the illustrative examples have been synthesised according to this proceeding, in compounds 19 to 25, $R'_2=H$ and R is as defined hereinbelow:

compound 19 R =OH
compound 20 R =Cl

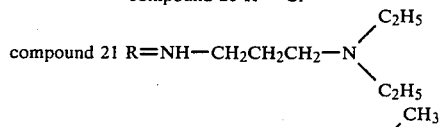

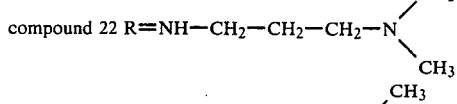

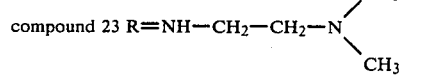

compound 24 R=NH—CH—(CH$_2$)$_3$—N(C$_2$H$_5$)$_2$
                    |
                    CH$_3$ compound 25 R=NH—CH$_2$—CH$_2$—CH$_2$—NH$_2$ ; in
compound 26 R$_2'$=CH$_3$
and R=OH According to this proceeding, the product of formula 15, which is a starting material according to the process of the invention and which may be in its tautomeric form (15a).

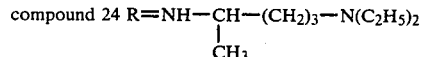

(15)

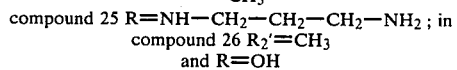

(15a)

may be prepared from cinnamic acid of formula (12), by the process which comprises the steps of forming the corresponding azide (13); of effecting a cyclisation to form the corresponding isoquinoline and finally of eliminating the protector group of the amino group to obtain the 5-methyl-6-amino-isoquinolone of formula (15). The proceeding 2 is then carried out according to the process defined previously to obtain the compound according to the invention of formula XIX in which R is the hydroxy group (compound 19). The hydroxy group of this compound may then be substituted by an atom of chlorine, an amino group, such as for example the following groups, to obtain compounds 19 to 26.

—NH—(CH$_2$)$_3$—N$\begin{smallmatrix}C_2H_5\\C_2H_5\end{smallmatrix}$

—NH—(CH$_2$)$_n$—N$\begin{smallmatrix}CH_3\\CH_3\end{smallmatrix}$   n = 2 or 3

—NH—CH—(CH$_2$)$_3$—N$\begin{smallmatrix}C_2H_5\\C_2H_5\end{smallmatrix}$
    |
    CH$_3$

—NH—CH$_2$—CH$_2$—CH$_2$—NH$_2$

The cinnamic acid of formula (12) used as starting product in proceeding n°2 defined hereinabove may be obtained in different ways. Three proceedings will be indicated hereinafter which are suitable for obtaining the cinnamic acid of formula (12) [proceedings (a) to (c)]

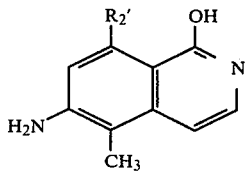

(10a)   (10b)   (11)

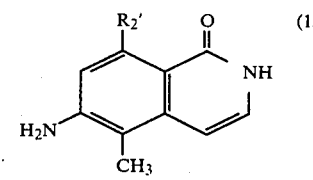

(12)

$R'_2$ being as defined previously.

According to this proceeding, the cinnamic acid of formula (12) is obtained from the 2-methyl-3-amino-benzonitrile of formula (10a) by the process which comprises the steps of converting the amino group of this compound into the acetylamino group to form the compound of formula (10b); of converting the cyano group of the 2-methyl-3-acetylamino-benzonitrile into the aldehyde group to form the compound of formula (11) and then of condensing the aldehyde group of this latter compound with malonic acid to form the cinnamic acid of formula (12). This proceeding is illustrated by example 5 hereinafter.

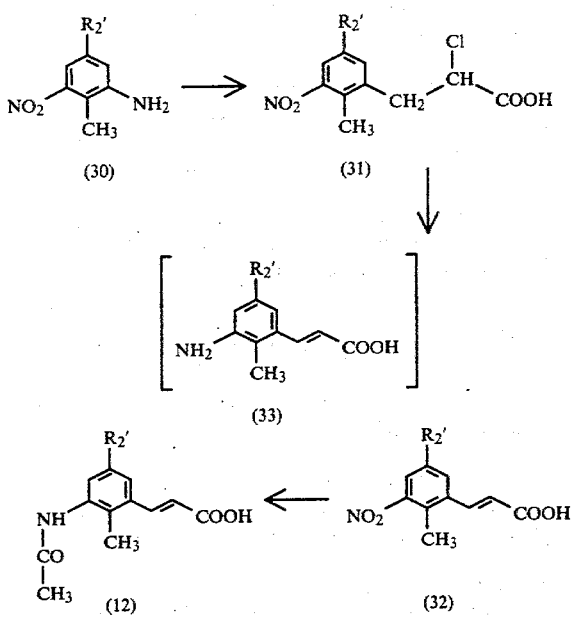

R'₂ being as defined previously.

This proceeding comprises the steps of converting 2-methyl-3-nitroaniline of formula (30) into (2-methyl-3-nitro-phenyl) chloropropionic acid of formula (31), of converting this latter compound into 2-methyl-3-nitro-cinnamic acid of formula (32) by elimination of HCl and then in converting the nitro group of this compound into the acetylamino group, passing through the stage of the amino group (formula 33) to form the compound of formula (12).

This proceeding will be illustrated by example 13 hereinafter.

PROCEEDING (C)

This proceeding is suitable for obtaining the compound of formula (12) in which R'₂ is—CH₃

(A) into an aldehyde group [compound of formula (B)], of condensing this aldehyde group with malonic acid to form the cinnamic acid of formula (C), of reducing the nitro group of the compound of formula (C) into an amino group [compound of formula (D)] which is then converted into the acetylamino group to obtain the compound of formula (12). This proceeding will be illustrated by example 12 hereinafter.

The intermediate compounds obtained when carrying out proceeding n°2 hereinabove and proceedings (a), (b) and (c), are within the scope of the invention, as well as their isomeric and tautomeric forms when they exist.

Among the compounds of the present invention, particular mention may be made of the following:

5,11-dimethyl-dipyrido [4,3-b][3,4-f] indole;

2,5,9,11-tetramethyl dipyrido [4,3-b][3,4-f] indolinium diacetate;

5,11-dimethyl-dipyrido [4,3-b][3,4-f] indole acetate.

5,11-dimethyl-dipyrido [4,3-b][3,4-f] indole dihydrochloride.

1,2-dihydro-1-oxo-4-methyl dipyrido [4,3-b][3,4-f] indole;

1-chloro, 5-methyl dipyrido [4,3-b][3,4-f] indole;

1-(α-diethylaminopropyl)amino-55-methyl-dipyrido [4,3-b][3,4-f] indole;

1-(α-dimethylaminopropyl)amino-5-methyl-dipyrido [4,3-b][3,4-f]indole;

1-(β-dimethylaminoethyl)amino-5-methyl-dipyrido [4,3-b][3,4-f]indole;

1-[α-methyl(δ-diethylamino butyl)amino]-5-methyl-dipyrido [4,3-b][3,4-f]indole;

1-[(Γ-amino-propyl)amino]-5-methyl-dipyrido [4,3-b][3,4-f]indole;

1,2-dihydro-1-oxo-5,11 dimethyl-dipyrido [4,3-b][3,4-f]indole.

The invention also relates to antiviral and antitumoral pharmaceutical compositions containing a therapeutically effective quantity of a compound according to the invention of formula II, in combination with a pharmaceutically inert excipient. The pharmaceutical composi-

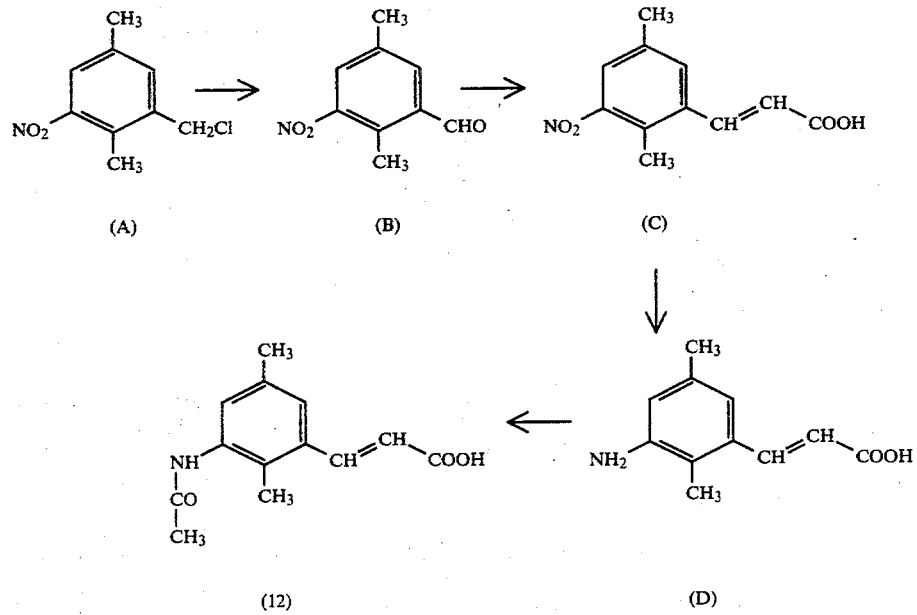

This proceeding comprises the steps of converting the chloro-methyl group of the compound of formula tions according to the invention may be particularly in the form of solutions injectable by the intravenous (i.v.) or intramuscular (i.m.) route.

The antitumoral properties of the compounds according to the invention have been determined by their curative action on inoculated test L-1210 leukemia. This leukemia has in fact enabled numerous active compounds used in human therapeutics to be selected. [ZUBROD C. G., Proc. Nat. Acad. Sci. 1972, 69, 1042–1047 and SCHEPARTZ SA. SCREENING, 1971, CANCER Chemother. Rep. Part 3 vol.2 p.3].

This leukemia is maintained in ascitic form by passage (i.p. route) on CBD1 (C57 B16 × DBA/2)Fl mice. The preparations to be tested are injected by the intraperitoneal route at least one day after the incoculation of the cells (one injection only). The results are expressed in increased life span percent(ILS %) according to KESSEL et al. Cancer Res. 1971, 31, 1883–1887) or in percentage of the number of cells killed by the product (the survival of the animals is proportional to the number of cells injected).

The protective power of the compounds according to the invention have also been sought on the Friend viro-induced leukemia (J. Exp. Med. 1957-105 -307-318) and it has been determined that the compounds according to the invention are antiviral and antitumoral agents.

The study of the development of the MOLONEY viro-induced sarcoma (Nat. Cancer. Inst. Monograph 22, 139–142,1966) has also made it possible to determine that the compounds according to the invention are antiviral and antitumoral agents.

The toxic dose and the acute toxicity in vivo, i.e. the lethal doses LD 100 and LD 50, have also been determined.

Furthermore, it has been shown that the compounds according to the invention are cytotoxic at concentrations included between 0.2 and 10μm. and that compound 21 according to the invention is just as active, or more so, than products presently used as antitumoral agents.

The invention will now be illustrated by the following non-limiting examples.

EXAMPLE 1

Preparation of 5,11-dimethyl dipyrido [4,3-b][3,4-f] indole (compound of formula 8)

A-5,8-dimethyl 6-[4'(3'-nitro-pyridyl)amino]isoquinoline of formula (5).

36g of 5,8-dimethyl-6-amino-isoquinoline of formula (4) were dissolved in 1.5 of 1,2-dimethoxy-ethane; 33.14 g of 3-nitro-4-chloro-pyridine of formula (3) were added, then 95.85 ml of a solution of dry hydrochloric acid in ether assayed at 4.363 M [2 molar equivalents with respect to the amino-isoquinoline of formula (3)] were added.

After 192 hours of heating with reflux, the solvent was evaporated, the residue was taken up with 1.5 l of water with stirring for 1 hour and the insoluble precipitate was filtered off to give 1.7 g of 3-nitro-4-hydroxy-pyridine.

With constant checking with a pH meter, potassium carbonate was progressively added to the aqueous phase and the precipitate which appears from pH 4 was filtered off when pH 5.5 was reached. After drying, said precipitate was recrystallised from benzene and 17.6 g or 28.6%, of yellow micro-crystals were thus obtained, melting point 206° C., corresponding to the expected compound.

| Analysis: $C_{16}H_{14}N_4O_3$ | C | H | N |
|---|---|---|---|
| % calculated | 65.29 | 4.80 | 19.04 |
| % found | 65.09 | 4.81 | 18.86 |

By making alkaline the mother liquors up to pH 10, 13 g or 36%, of the amino-isoquinoline of formula (4), were recovered, melting point: 140° C. after crystallisation.

B/5,8-dimethyl-6-[4'-(3'-amino-pyridyl)amino]-isoquinoline of formula (6).

20g of nitrated derivative of formula (5) were dissolved in 1 liter of absolute ethanol, to which were added 2 g of 10% palladium charcoal and the whole was stirred in a hydrogen atmosphere at ambient pressure and temperature until the theoretical quantity of hydrogen has been absorbed. After filtration of the catalyst, the solvent was evaporated and the residue recrystallised from ethanol to give 16.9 g (93.7%) of beige crystals, melting point =235°–250° C. with decomposition, corresponding to the expected compound crystallised with ½ mole of ethanol.

| Analysis: $C_{16}H_{16}N_4, \frac{1}{2}C_2H_5OH$ | C | H | N |
|---|---|---|---|
| % calculated | 71.05 | 6.66 | 19.50 |
| % found | 70.78 | 6.77 | 19.18 |

C/1-(5',8'-dimethyl-isoquinolyl)][4,5-c]triazolo pyridine of formula (7).

16.8 g of the amine of formula (6) were dissolved in 300 ml of acetic acid, cooled to about 0° C. and 4.83g of sodium nitrite dissolved in 150 ml of water were progressively added thereto, drop by drop and in maintaining the cold. The reaction mixture was maintained cold, under stirring, for 2 hours, then 1 hour allowing it to return to ambient temperature; the solent was evaporated, the residue was taken up with 300 ml of water and the insoluble precipitate was filtered.

After recrystallisation from ethanol, 14.8 g (84.5%) of pale yellow crystals were formed, melting point 215°–220° C., corresponding to the expected product.

| Analysis: $C_{16}H_{13}N_5$ | C | H | N |
|---|---|---|---|
| % calculated | 69.80 | 4.76 | 25.44 |
| % found | 69.67 | 4.77 | 25.23 |

D/5,11-dimethyl-dipyrido [4,3-b][3,4-f]indole of formula (8)

12 g of the triazolopyridine of formula (7) were mixed with 39 g of paraffin with a melting point of 54°–56° C. and the whole was heated under a nitrogen atmosphere until the gaseous emission was complete i.e. for 20 to 25 minutes.

After having left the reaction mixture to cool, 100 ml of heavy petroleum ether (boiling point under normal pressure: 100°–140° C.), were added, the mixture was heated up to boiling and the insoluble black solid was filtered off. This latter was taken up with ethanol in the presence of animal charcoal, filtered, concentrated and filtered in the cold, then recrystallised from pyridine to give 5.4 g (40.6%) of yellow micro-crystals, non-melting at 350° C.

| Analysis: $C_{16}H_{13}N_3$ | C | H | N |
|---|---|---|---|
| % calculated | 77.71 | 5.30 | 16.99 |
| % found | 77.52 | 5.32 | 16.98 |

EXAMPLE 2

Preparation of 2,5,9,11-tetramethyl-dipyrido[4,3-b][3,4-f]indolinium of formula IX[X=CH$_3$COO].

274 g of the compound of formula (8), obtained according to example 1, were suspended in 750 ml of acetone and heated with reflux for 6 hours, in the presence of a large excess of methyl iodide (1,42 g). After addition of the same quantity of methyl iodide, heating was again effected with reflux for 14 hours; the reaction mixture was then cooled and 487 mg (92%) of the insoluble product corresponding to the diiodide [compound of formula (IX) in which X=I] were filtered off.

| Analysis: $C_{18}H_{19}I_2N_3$ | C | H | N |
|---|---|---|---|
| % calculated | 40.68 | 3.58 | 7.91 |
| % found | 40.55 | 3.67 | 7.88 |

450 mg of the compound obtained, previously dissolved in 100 ml of water, were passed over an exchange resin column ("DOWEX 1X2") containing acetate ions and the solvent was evaporated. The residue was taken up with isobutyl alcohol to give the expected product in the form of yellow-orange microcrystals, melting point 230°–235° C. It gave one stain by chromatography on a thin alumina layer with the methanol-water mixture (4/11 v/v) as eluent; the nuclear magnetic resonance (NMR) spectrum indicates that it is the expected compound, but its centesimal analysis corresponds to the desired product partially hydrated.

EXAMPLE 3

Preparation of 5,11-dimethyl dipyrido-[4,3-b][3,4-f] indole.

1 g of the compound of formula (8), obtained according to example 1, and 20 ml of acetic acid were heated at boiling point and the excess of acetic acid was immediately evaporated. The residue, taken up with acetone and filtered yielded 1 g of insoluble precipitate in the form of yellow ochre micro-crystals, non-melting at 310° C., and corresponding to the monohydrate of the expected compound.

| Analysis: $C_{18}H_{19}N_3O_3$ | C | H | N |
|---|---|---|---|
| % calculated | 66.44 | 5.89 | 12.92 |
| % found | 66.58 | 5.83 | 12.79 |

EXAMPLE 4

5,11-dipyrido-[4,3-b][3,4-f]-indole dihydrochloride 200 mg of the base of formula (8) obtained according to example 1 were dissolved in 20 ml of absolute ethanol, 1 ml of ethanol saturated by hydrochloric acid was added and the solvent was evaporated in a water bath under reduced pressure. The residue was taken up with acetone and filtered off to yield 200 mg of ochre microcrystals, non-melting at 310° C. and corresponding to the expected dihydrochloride in the form of monohydrate.

| Analysis: $C_{16}H_{17}Cl_2N_3O$ | C | H | Cl | N |
|---|---|---|---|---|
| % calculated | 56.80 | 5.02 | 21.01 | 12.43 |
| % found | 56.34 | 4.78 | 21.20 | 12.56 |

EXAMPLE 5

Preparation of 1,2-dihydro-1-oxo5-methyl-dipyrido-[4,3-b][3,4-f] indole (compound 19).

(A) 2-methyl-3-acetylamino-benzaldehyde of formula (11)

39g (0.3 mole) of 2-methyl-3-amino-benzonitrile were dissolved in 75 ml of acetic acid, 30 ml (0.3 mole) of acetic anhydride were added, the mixture was heated with reflux for 5 minutes, and cooled. The solid obtained was filtered off and the evaporation of the solent furnished an additional quantity of solid which was added to the preceding one. After recrystallisation of the whole from toluene, 44 g (95%) of colorless flakes were obtained, with a melting point of 160° C. l

| Analysis: $C_{10}H_{10}N_2O$ | C | H | N |
|---|---|---|---|
| % calculated | 68.95 | 5.79 | 16.08 |
| % found | 68.82 | 5.83 | 15.99 |

(B) 2-methyl-3-acetylamino-cinnamic acid of formula (12)

In a 6l three-necked flask were introduced 60 g (0.34 mole) of the nitrile of formula (10) and 1 liter of 50% diluted formic acid, then the mixture was heated at boiling point. Maintaining the whole with reflux, 120 g of Raney alloy were added at 5 times, at intervals of 30 minutes; the mixture was left 30 minutes more at reflux and the salts and the excess of insoluble reagent were filtered.

The precipitate was washed in hot water and the whole of the filtrate was extracted with chloroform, at least ten times with 500 ml of chloroform each time.

The evaporation of the organic phase gave a residue which distilled, giving 39 g of a product (boiling point 11=210°–225° C.) corresponding to the mixture of the starting nitrile and the aldehyde of formula (11), i.e. the 2-methyl-3-acetylamino-benzaldehyde. If crystallisation was effected from benzene or toluene, fine, colorless needles were obtained, melting point: 124°–128° C.

| Analysis: $C_{10}H_{11}NO_2$ | C | H | N |
|---|---|---|---|
| % calculated | 67.78 | 6.26 | 7.91 |
| % found | 68.07 | 6.27 | 8.05 |

The preceding mixture (38 g), crude from distillation, was dissolved in 50 ml of dry pyridine; it was added all at once to a solution of 300 ml of pyridine containing 22.5 g of malonic acid and 1 ml of piperidine, and the whole was heated with reflux for 1½ hours. The pyridine was evaporated under reduced pressure and the residue was treated by a solution of sodium hydroxide in excess in the presence of chloroform.

After decantation, the evaporation of the chloroform gave a residue constituted by a fraction of starting nitrile of formula (10).

The acidification of the alkaline layer by hydrochloric acid gave the acrylic acid of formula (12), which was recrystallised from acetic acid, giving 25g (34% with respect to the quantity of nitrile of formula (10) used of colorless flakes, melting point=265°–267° C.

| Analysis: $C_{12}H_{13}NO_2$ | C | H | N |
| --- | --- | --- | --- |
| % calculated | 65.74 | 5.98 | 6.39 |
| % found | 65.58 | 6.12 | 6.52 |

(C) 2-methyl-3-acetylamino-cinnamoylazide of formula (13)

The acrylic acid of formula (12) (36 g) was added to a solution of 17 g of triethylamine in 150 ml of acetone and the whole was cooled up to 0° C. Maintaining the temperature below 0° C., a solution of 24.3 g of ethylchloroformate in 150 ml of acetone was added drop by drop, the mixture was stirred at 0° C. for 1 hour, then the solution formed from 16 g of sodium azide and 40 ml of water was progressively added. The reaction mixture was again stirred in the cold for 1 hour after the end of the addition and 27.8 g(71%) of a colorless solid corresponding to the desired azide which was decomposed by melting from 150° C., were filtered off. The evaporation of the acetone of the mother liquors in a water bath under reduced pressure, and not exceeding 30° C. gave an additional quantity of the expected compound which was then colored yellow. This product was used in the synthesis without any other purification.

(D) 1-hydroxy-5-methyl-6-acetylamino-isoquinoline or 5-methyl-6-acetylamino-1-isoquinolone of formula (14).

The mixture constituted by 1.5l of diphenyl ether and 33 g of tributylamine was heated to 240° C. in a 4l, three-necked flask. 41g of the azide of formula (13) previously dried in a vacuum desiccator were placed in suspension in 300 ml of diphenyl ether and the mixture was added to the preceding solution maintained under violent stirring, in small portions but as rapidly as possible and continuing to heat to avoid the temperature dropping to below 220° C.

After the end of the addition, heating was again effected to 240° C. and the reaction mixture was maintained at this temperature for 10 minutes, then it was left to cool. The precipitate formed was filtered, washed in benzene and recrystallised from ethanol, in which it was very sparingly soluble, to give 25 g (69%) of colorless microcrystals, non-melting at 320° C.

| Analysis: $C_{12}H_{12}N_2O_2$ | C | H | N |
| --- | --- | --- | --- |
| % calculated | 66.65 | 5.59 | 12.96 |
| % found | 66.98 | 5.64 | 12.87 |

(E) 5-methyl-6-amino-1-isoquinolone of formula (15)

The mixture formed by 500 ml of ethanol, 100 ml of hydrochloric acid and 25 g of the compound of formula (14) was heated with reflux for 2½ hours. The evaporation of the solvent gave a residue which was taken up with hot water, filtered, and the alkalinisation of the filtrate by N sodium hydroxide gave 16.3 g (81%) of a compound which recrystallised in the form of colorless needles, melting point=260°–285° C. with decomposition.

| Analysis: $C_{10}H_{10}N_2O$ | C | H | N |
| --- | --- | --- | --- |
| % calculated | 68.95 | 5.79 | 16.08 |
| % found | 68.97 | 5.83 | 15.85 |

(F) 5-methyl-6-[4'-(3'-nitro-pyridyl)amino]1-isoquinolone of formula (16)

17.4 g of the compound of formula (15) were dissolved in 400 ml of dimethyl formamide (DMF); a solution of 15.9 g of chloronitro-pyridine of formula (3) in 100 ml of DMF was added and this mixture was left at ambient temperature for 12 days. The precipitate formed was filtered off; the evaporation of the solvent under reduced pressure gave an additional quantity of solid and the whole of said latter was taken up with hot water then rendered alkaline by N sodium hydroxide. The precipitate formed was recrystallised from DMF, giving 21.3g (72%) of yellow prisms non melting at 330° C. and corresponding to the compound of formula 16.

| Analysis: $C_{15}H_{12}N_4O_3$ | C | H | N |
| --- | --- | --- | --- |
| % calculated | 60.80 | 4.03 | 18.91 |
| % found | 60.46 | 4.08 | 18.62 |

When the reaction has been effected in the presence of an excess of 1 to 3% of the 3-nitro-4-chloro-pyridine of formula (3), apart from the product described hereinabove, from 10to 15% of a secondary product, less soluble in the DMF, was isolated, which was recrystallised from this solvent in the form of red prisms, non fusible at 330° C. It corresponds to 3-nitro-4-amino di [N-1, N-4(1'-hydroxy-5'-methyl-6'-isoquinolyl)pyridine].

| Analysis: $C_{26}H_{19}N_5O_4, \frac{1}{2}H_2O$ | C | H | N |
| --- | --- | --- | --- |
| % calculated | 64.95 | 4.35 | 14.38 |
| % found | 64.72 | 4.19 | 14.28 |

(G) 5-methyl-6-[4'-(3'-amino-pyridyl)amino]isoquinolone of formula (17)

12.6 g of the preceding nitrated derivative were dissolved in 500 ml of acetic acid; 0.6 g of 10% palladium charcoal was added and stirring was effected under a hydrogen atmosphere until the theoretical quantity of hydrogen was absorbed. 500 ml of acetic acid were added, the mixture was heated to dissolve the precipitate formed, the catalyst was filtered, the solvent was evaporated and the residue was dissolved in water. After alkalinisation up to pH 9, the precipitate was filtered and recrystallised in acetonitrile to give 10.2 g (84.3%) of cream micro-crystals, corresponding to the hydrate of the amine of formula (17).

| Analysis: $C_{15}H_{16}N_4O_2$ | C | H | N |
| --- | --- | --- | --- |
| % calculated | 63.86 | 5.67 | 19.71 |
| % found | 63.84 | 5.44 | 19.47 |

(H)
1-[6'-(1',2'-dihydro-1'-oxo-5'-methyl-isoquniolyl)]-triazolo [4,5-c]-pyridine of formula (18).

In a 500 ml, three-necked flash provided with a thermometer, a mechanical stirrer and a dropping funnel, 10.2 g of the amine of formula (17) and 70 ml of acetic acid were mixed; the reaction mixture was cooled up to about 0° C. and a solution of 3 g of sodium nitrate in the minimum of water was progressively added. Stirring was continued for 1 hour, allowing the reaction mixture to return to ambient temperature; the precipitate was then filtered, washed in water and dried. 8.3 g (83.5%) of colourless microcrystals were thus obtained; melting point 309°–310° C., corresponding to the hydrate of the triazolopyridine of formula (18).

| Analysis: $C_{15}H_{15}N_5O_2$ | C | H | N |
|---|---|---|---|
| % calculated | 61.01 | 4.44 | 23.72 |
| % found | 60.92 | 4.15 | 23.44 |

(I) 1,2-dihydro-1-oxo-5-methyl-dipyrido [4,3-b][3,4-f]indole of formula XIX with R=OH: compound 19

8 of triazolopyridine of formula (18) were added to 60 g of melted phenanthrene, then heated to 340° C., and the reaction mixture was maintained under stirring at this temperature for 20 minutes, then left to cool. The phenanthrene was extracted with petroleum ether or hexane and the insoluble residue was recrystallized from DMF to give 4.2 g (58%) of grey micro-crystals non-fusible at 310° C. and corresponding to the hemi-hydrate of the product of formula (19).

| Analysis: $C_{15}H_{11}N_3O, \frac{1}{2} H_2O$ | C | H | N |
|---|---|---|---|
| % calculated | 69.75 | 4.68 | 16.27 |
| % found | 70.04 | 4.40 | 16.14 |

EXAMPLE 6

1-chloro-5-methyl-dipyrido [4,3-b][3,4-f] indole (compound of formula XIX with R=Cl: compound 20)

1.5 g of the dipyrido-indole (compound 19) was mixed with 250 ml of phosphorus oxychloride containing 1.5 g of phosphorus pentachloride and the mixture was heated with reflux for 20 hours. The excess of oxychloride and pentachloride was eliminated in a water bath under reduced pressure and the residue was taken up with tepid water, on several times and in stirring on each time for 1 hour, until exhaustion. The aqueous filtrates combined and cooled were neutralised by a solution of sodium or potassium carbonate and the precipitate formed, filtered off then dried, was recristallised from DMF, giving 875 mg (54%) of yellow microcrystals, non-melting at 320° C. and corresponding to the hemi-hydrate of the chlorinated derivative 20.

| Analysis: $C_{15}H_{10}N_3Cl, \frac{1}{2}H_2O$ | C | H | N | Cl |
|---|---|---|---|---|
| % calculated | 65.10 | 3.97 | 15.19 | 12.84 |
| % found | 64.77 | 3.92 | 14.97 | 13.21 |

EXAMPLE 7

1-Γ-diethylaminopropyl)amino-5-methyl-dipyrido-[4,3-b][3,4-f] indole (compound of formula XIX with

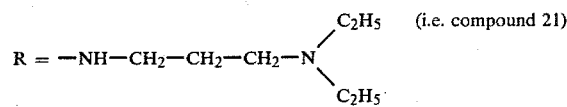

The mixture, constituted by 875 mg of the chlorinated derivative obtained according to example 6 hereinabove and 10 g of Γ-diethyl-aminopropylamine, was heated in an oil bath at 150° C. for 30 minutes and the excess of amine was eliminated in a water bath under reduced pressure. The residue was extracted three times with 60 ml of boiling benzene and the insoluble residue was taken up with chloroform in the presence of sodium hydroxide. After washing of the chloroform layer in water, the chloroform was evaporated, the residue was taken up with the benzene previously used and the whole was concentrated up to about 50 ml and cooled. The filtration of the solid in suspension gave 180 mg (15%) of yellow microcrystals, melting point=215°–218° C., corresponding to the expected amine crystallized with a molecule of water.

| Analysis: $C_{22}H_{27}N_5,H_2O$ | C | H | N |
|---|---|---|---|
| % calculated | 69.63 | 7.70 | 18.46 |
| % found | 70.02 | 7.39 | 18.29 |

It has been ascertained that by operating with an excess of Γ-diethylaminopropylamine, the yield may be improved. According to this embodiment, the mixture, constituted by 4 g of the chlorinated derivative obtained according to example 6 hereinabove and 100 ml of Γ-diethylaminopropylamine, was heated with reflux for 4 hours and the excess of amine was eliminated under reduced pressure. The residue obtained was taken up with a N sodium hydroxide solution and the precipitate formed, filtered off and dried, was recrystallised from xylene to give 4.1 g (73%) of the expected derivative which has crystallized with a molecule of water.

| Analysis: $C_{22}H_{27}N_5,H_2O$ | C | H | N |
|---|---|---|---|
| % calculated | 69.63 | 7.70 | 18.45 |
| % found | 69.82 | 7.49 | 18.33 |

EXAMPLE 8

1-(Γ-dimethylaminopropyl)amino-5-methyl-dipyrido-[4,3-b][3,4-f] indole (compound of formula XIX)

$$R = -NH-CH_2-CH_2-CH_2-N\begin{matrix}CH_3\\ \\CH_3\end{matrix} \quad \text{(compound 22)}$$

The procedure according to the first proceeding described in example 7 was carried out, in heating at boiling point dimethylamine-propylamine for 7 hours. After a treatment identical to the one mentioned hereinabove, the product was recrystallized from benzene to give pale yellow micro-crystals, melting point: 240° C., corresponding to the hemi-hydrate of the expected product.

| Analysis: $C_{20}H_{23}N_5$, ½ $H_2O$ | C | H | N |
|---|---|---|---|
| % calculated | 70.09 | 7.00 | 20.44 |
| % found | 70.27 | 6.85 | 20.13 |

By operating according to the embodiment described in example 7 hereinabove, a yield of 73% has been obtained. According to this embodiment, the chlorinated derivative of example 6 with a large excess of Γ-dimethylaminopropylamine was heated with reflux for 4 hours. After elimination of the excess of amine under reduced pressure, the product was recrystallised from benzene and 73% of micro-crystals were obtained, the melting point of which is 240° C.; this product corresponds to the hemi-hydroxide of the expected product.

1 g of the compound obtained hereinabove was dissolved in 30 ml of ethanol saturated by hydrochloric acid, the mixture was heated to boiling point and cooled immediately. The precipitate formed is recrystallized from ethanol and 1 g of colourless needles was obtained, melting point=266°–268° C., corresponding to the hydrated tri-hydrochloride of compound 22 hereinabove.

| Analysis: $C_{20}H_{23}N_5$, 3HCl, $H_2O$ | C | H | N | Cl |
|---|---|---|---|---|
| % calculated | 52.11 | 6.08 | 15.20 | 23.12 |
| % found | 51.72 | 6.21 | 14.83 | 22.88 |

EXAMPLE 9

1-(β-dimethylaminoethyl)amino-5-methyl-dipyrido-[4,3-b][3,4-f] indole (compound of formula XIX)

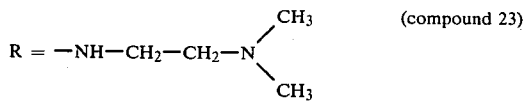

(compound 23)

The procedure was the same as in examples 7 and 8 above, in heating the chlorinated compound 20, in β-dimethylaminoethylamine at boiling point for 15 hours. After a treatment identical to those mentioned in the two preceding cases, the product was recrystallised, then taken up with hydrochloric ethanol to form the corresponding trihydrochloride, which was recrystallised from ethanol in colourless prisms, melting point 262°–269° C., corresponding to the dihydroxide of the trihydrochloride of the expected compound 23 : $C_{19}H_{21}H_5$. Yield 37%.

| Analysis: $C_{19}H_{21}N_5$, 3HCl 2 $H_2O$ | C | H | N | Cl |
|---|---|---|---|---|
| % calculated | 49.08 | 6.02 | 15.07 | 22.93 |
| % found | 49.58 | 5.77 | 14.52 | 23.26 |

EXAMPLE 10

1-[(α-methyl-δ-diethylamino-butyl)-amino]-5-methyl-dipyrido-[4,3b][3,4-f] indole (compound of formula XIX with R=NH—CH—CH₂—CH₂—CH₂—N(C₂H₅)₂ i.e. compound 24).

500 mg of the chlorinated derivative obtained according to example 6 hereinabove were placed in 10 ml of 2-amino-5-diethylamino-pentane and the mixture was heated with reflux of the amine for 13 hours, under a nitrogen atmosphere and protected from the light. The excess of amine was eliminated and the residue was taken up with a N sodium hydroxide solution. The precipitate formed was filtered off, washed in water, dried and recrystallised from toluene to give 120 mg (17%) of yellow micro-crystals, melting at around 160° C.

| Analysis: $C_{24}H_{31}N_5H_2O$ = 405.5 | C | H | N |
|---|---|---|---|
| % calculated | 71.08 | 7.71 | 17.22 |
| % found | 70.78 | 7.94 | 17.59 |

EXAMPLE 11

1-[(γ-amino-propyl)amino]-5-methyl-dipyrido [4,3-b][3,4-f] indole.

(Compound of formula XIX with R=NH—CH₂—CH₂—CH₂—NH₂ i.e. compound 25).

The procedure is the same as in example 7 with 400 mg of the chlorinated derivative obtained according to example 6 and 10 ml of 1,3-diamino-propane, in heating with reflux for 1 hour. The excess of 1,3-diamino-propane was eliminated, the residue was taken up with a N-sodium hydroxide solution and the precipitate was filtered off. This latter was recrystallised from dimethylformamide to give 190 mg (42%) of pale yellow micro-crystals, melting point=268°–269° C.

| Analysis: $C_{18}H_{19}N_5, 0.33$ $H_2O$ = 311 | C | H | N |
|---|---|---|---|
| % calculated | 69.45 | 6.32 | 22.51 |
| % found | 69.33 | 6.50 | 22.43 |

EXAMPLE 12

Preparation of 1,2-dihydro-1-oxo-5,11-dimethyl-dipyrido-[4,3-b][3,4-f] indole (compound of formula L: compound 26).

The general schema of the synthesis of this compound is shown hereinafter. This synthesis was carried out according to the proceeding (c) to obtain the compound of formula E (reactions 1 to 4) which is a particular compound of general formula (12) and according to proceeding n°2 (reactions 5 to 11). Compound (G) to (L) hereinafter may be presented in tautomeric form.

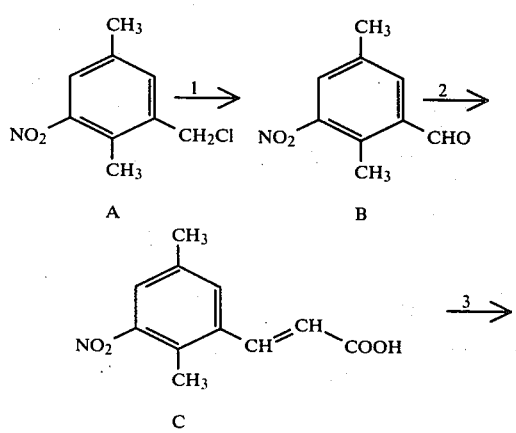

| Analysis: $C_{11}H_{11}NO_4 = 221.21$ | C | H | N |
|---|---|---|---|

2,5-dimethyl-3-acetylamino-trans cinnamic acid (E)

141 g of nitrocinnamic acid of formula C were suspended in 1260 ml of acetic acid; 170 g of Raney nickel washed in acetic acid and hydrogen were added to this mixture, the mixture being stirred in a hydrogen atmosphere under normal pressure until cessation of absorption of said hydrogen. (The theoretical quantity was absorbed). Hot filtration was effected to eliminate the catalyst and half of the acetic acid was evaporated.

A small sample was evaporated to dryness, taken up with water, neutralised in ammonia, filtered off and recrystallised from ethanol to obtain colourless microcrystals corresponding to 2,5-dimethyl-3-amino-trans cinnamic acid of formula D, melting point 185° C.

| Analysis: $C_{11}H_{13}NO_2, \frac{1}{2} H_2O = 200.23$ | C | H | N |
|---|---|---|---|
| % calculated: | 65.98 | 7.05 | 7.00 |
| % found | 65.62 | 6.82 | 7.07 |

To the rest, coming from the evaporation of half of the acetic acid, 150 ml of acetic anhydride were added, the resulting mixture was heated with reflux for 1½ hours then evaporated to dryness. The solid residue was taken up with hydrochloric water, stirred for 1 hour and filtered off to give a solid which was recrystallised from acetic acid, giving 126.2 g (84%) of colourless flakes corresponding to the acid of formula E, melting point 270° C.

| Analysis: $C_{13}H_{15}NO_3 = 233$ | C | H | N |
|---|---|---|---|
| % calculated | 66.93 | 6.48 | 6.01 |
| % found | 66.78 | 6.51 | 6.11 |

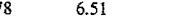

2,5-dimethyl-3-acetylamino-trans cinnamoylazide (F)

The mixture formed by 125 g of cinnamic acid E, 1.1 liter of acetone and 54 g of triethylamine was cooled up to 0° C., then 78.8 g of ethyl-chloroformate dissolved in 460 ml of acetone were progressively added with stirring and maintaining the temperature at 0° C. Stirring was continued for one hour at 0° and in continuing to cool to maintain the temperature below 5° C., a solution of 52.5 g of sodium azide in the minimum of water was added. After the end of the addition, stirring was again effected for 1 hour at 0° C., the mixture was allowed to return to ambient temperature, then poured in 5 l of water and the precipitate formed was filtered off. This latter was washed abundantly in water, in terminating the washing with distilled water, then with a little acetone and finally dried to obtain 107 g (77%) of fine cottony needles which melt from 150° C. and present one stain only in thin layer chromatography on silica gel. This compound F is used as such in the following synthesis.

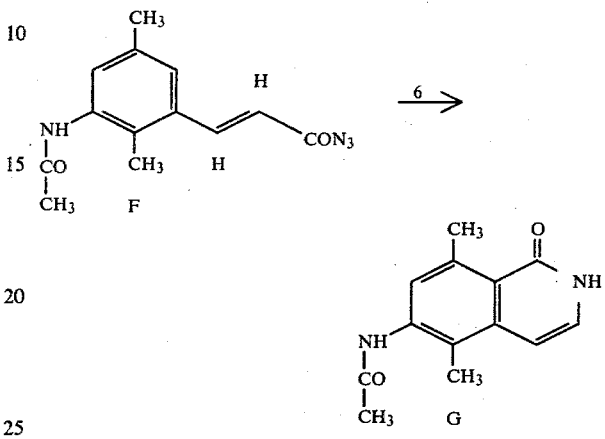

1,2-dihydro-1-oxo-5,8-dimethyl-6-acetylamino-isoquinoline(G)

To the mixture constituted by 500 ml of diphenylether and 28.6 g of tributylamine heated at 240° C. and maintained under violent stirring, were progressively added, in 15 minutes, 39.6 g of azide in suspension in 450 ml of diphenylether maintained at 40° C., care being taken that the temperature does not drop below 235° C. After the end of the addition, stirring was effected for a further 15 minutes at 240° C. then the mixture is allowed to cool, eliminating part of the diphenyl ether under vacuum. The crystallisation of a solid was observed, 350 ml of benzene were added and the precipitate was filtered off. Said latter was taken up with 400 ml of boiling ethanol and the insoluble fraction, filtered off, was recrystallised from 400 ml of dimethylformamide, unfiltering hot, to obtain 18.7 g (53%) of colourless flakes corresponding to compound G.

| Analysis: $C_{13}H_{14}N_2O_2 : 230.3$ | C | H | N |
|---|---|---|---|
| % calculated | 67.80 | 6.13 | 12.17 |
| % found | 67.54 | 6.42 | 11.96 |

1,2-dihydro-1-oxo-5,8-dimethyl-6-amino-isoquinoline (H)

The mixture consisting of 10.6 g of the compound G, 175 ml of ethanol and 35 ml of concentrated hydrochloric acid was heated with reflux for 2½ hours, 300 ml of water were added, the mixture was again heated to boiling point and filtered to eliminate a small insoluble fraction. To the cooled filtrate was added a N sodium

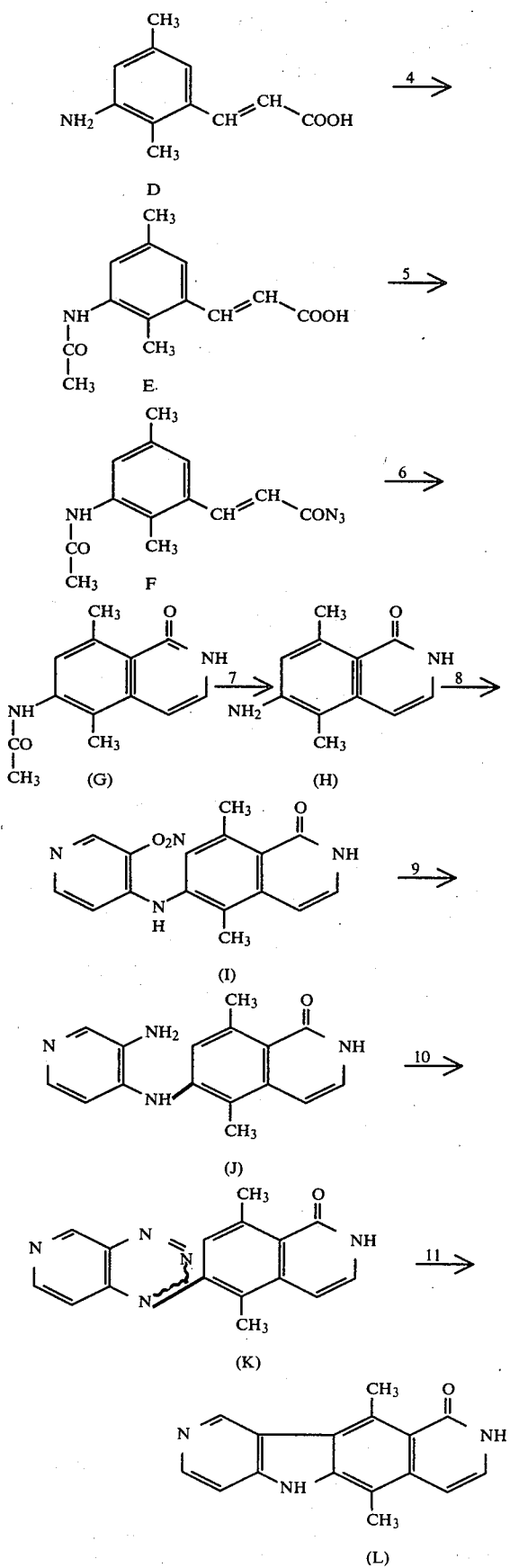

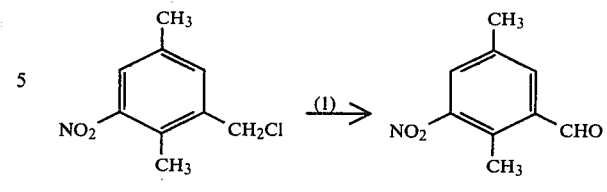

2,5-dimethyl-3-nitro-benzaldehyde (B)

The mixture constituted by 2,5-dimethyl-3-nitrobenzyl-chloride (A) prepared according to M. J. WINCHESTER and F. D. POPP, J. Het. Chem. 12, p. 547 (1975) (610 g), acetic acid (1280 ml), water (1280 ml) and hexamethylene tetramine (855 g) was heated with reflux under stirring for 2 hours. 1037 ml of concentrated hydrochloric acid were then added in 10 minutes and the mixture was again heated with reflux for 20 minutes. This mixture, cooled to 0° C., gave a solid which was filtered off, dried and recrystallised from cyclohexane (4 liters) to give 290.5 g (53%) of yellow needles corresponding to the aldehyde of formula B, melting point : =90°-93° C.

| Analysis: $C_9H_9NO_3 = 179$ | C | H | N |
|---|---|---|---|
| % calculated | 60.30 | 5.06 | 7.80 |
| % found | 60.13 | 4.97 | 7.71 |

2,5-dimethyl-3-nitro-trans cinnamic acid (C)

The mixture constituted by 193.7 g of aldehyde of formula B, 112.5 g of malonic acid, 1.5 l of pyridine dried on potassium hydroxide and 9 ml of piperidine was heated with reflux for 24 hours but adding, twice, 112.5 of malonic acid, after 3½ hours and 6 hours of reflux. After evaporation of the solvent, the residue was taken up with acetone, filtered off, washed in water and again in acetone to give the pure compound C, which was recrystallised from ethanol and gave ochre microcrystals, melting point : 228° C. Yield: 173 g (72%).

| Analysis: $C_{11}H_{11}NO_4 = 221.21$ | C | H | N |
|---|---|---|---|
| % calculated: | 59.72 | 5.01 | 6.33 |
| % found | 59.74 | 4.91 | 6.21 | hydroxide solution to bring the pH to 9 and the precipitate formed was filtered off then recrystallised from ethanol to give 7.35 g (85%) of cream flakes corresponding to the amine of formula H, melting point 242° C.

| Analysis: $C_{11}H_{12}N_2O = 188.2$ | C | H | N |
|---|---|---|---|
| % calculated | 70.18 | 6.43 | 14.88 |
| % found | 70.25 | 6.15 | 14.52 |

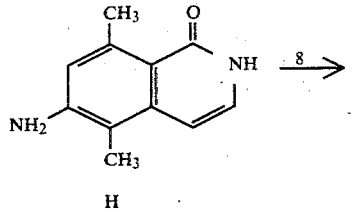

H $\xrightarrow{8}$

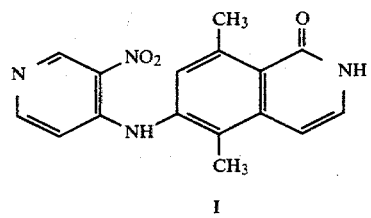

I 1,2-dihydro-1-oxo-5,8-dimethyl-6-[4'-(3'-nitro-pyridyl)amino] isoquinoline or
5,8-dimethyl-6-[4'-(3'-nitropyridyl)amino] isoquinoline (I)

The mixture consisting of 34.7 g of the amine of formula H, 27.3 g of 3-nitro-4-chloro-pyridine and 1 liter of dimethylformamide was stirred at ambient temperature for 15 days and the solvent was evaporated. The residue was taken up with 3 liters of N hydrochloric acid and the insoluble fraction was filtered off. It corresponds essentially to an undesirable secondary compound which recrystallised from dimethylsulfoxide in form of orange-red micro-crystals, non melting at 300° C.

| Analysis: $C_{27}H_{23}N_5O_4,H_2O = 499.5$ | C | H | N |
|---|---|---|---|
| % calculated | 64.92 | 5.04 | 14.02 |
| % found | 65.19 | 4.81 | 13.79 |

To the aqueous phase was added a N sodium hydroxide solution to bring the pH to 9–10 and the precipitate formed was filtered off, then recrystallised from dimethylformamide to give 22 g (39%) of yellow microcrystals corresponding to the compound of formula I, melting point 310°–315° C.

| Analysis: $C_{16}H_{14}N_4O_3 = 310.3$ | C | H | N |
|---|---|---|---|
| % calculated | 61.93 | 4.55 | 18.06 |
| % found | 61.53 | 4.71 | 17.76 |

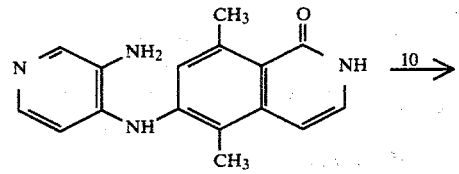

$\xrightarrow{10}$

J

| Analysis: $C_{16}H_{14}N_4O_3 = 310.3$ | C | H | N |
|---|---|---|---|

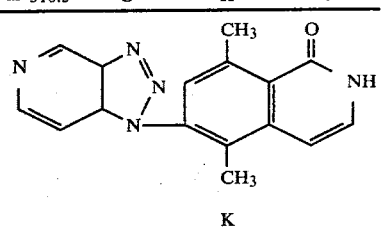

K 1,2-dihydro-1-oxo-5,8-dimethyl 6-[4'-(3'-amino-pyridyl)amino] isoquinoline J and 1-[6'-(14,2'-dihydro-1'-oxo-5',8'-dimethylisoquinolyl)] triazolo(4,5 c) pyridine (K)

To 16.8 g of nitrated derivative I in 1 liter of acetic acid were added 17 g of Raney nickel and hydrogen, stirring the whole under a hydrogen atmosphere at ambient temperature and at normal pressure. The theoretical quantity of hydrogen was absorbed in about 1 hour and the catalyst was filtered, then 50 ml of the resultant solution were taken.

By evaporating this solution, a residue was obtained which was taken up with water and rendered alkaline by the addition of a N-sodium hydroxide solution. The precipitate formed was filtered off, it was recrystallised from acetonitrile, then from anisole to obtain colourless micro-crystals corresponding to the amine of formula J, melting point 212°–215° C.

| Analysis: $C_{16}H_{16}N_4O$, $H_2O = 298$ | C | H | N |
|---|---|---|---|
| % calculated | 64.41 | 6.08 | 18.78 |
| % found | 64.14 | 5.83 | 18.83 |

The remaining solution was cooled to 14° C. and, with stirring, a solution of 3.61 g of sodium nitrite in the minimum of water was added with 15 minutes. Stirring was continued for 1½ hours, allowing the mixture to return to ambient temperature, the solvent was eliminated, the residue was taken up with water, filtered off and the precipitate washed in water. The solid obtained was taken up with 1.5 l of boiling ethanol, filtering was effected, then concentration to 600 ml to give, after cooling, 12g (80%) of cream microcrystals corresponding to the triazolopyridine of formula K, melting point 300°–302° C.

| Analysis: $C_{16}H_{13}N_5O = 291$ | C | H | N |
|---|---|---|---|
| % calculated | 65.97 | 4.5 | 24.04 |
| % found | 65.66 | 4.70 | 24.39 |

K $\xrightarrow{11}$ 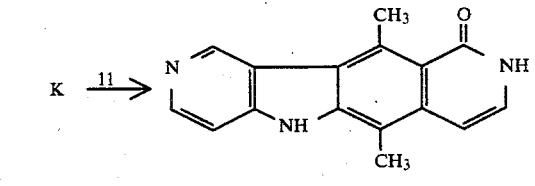

L 1,2-dihydro-1-oxo-5,11-dimethyl-dipyrido-[4,3-b][3,4-f] indole L 16g of triazolopyridine of formula K were mixed with 80 g of phenanthrene, and in maintaining the whole under stirring, the mixture was heated in a metal bath at 340° C. for 30 minutes, after which time the emission of nitrogen substantially stopped. Heating was then effected at 360° C. for 2 minutes, the mixture was allowed to cool and poured in 600 ml of hexane. The insoluble precipitate was filtered off, washed in boiling hexane, then recrystallised from dimethylformamide to give 5.7g (36.5%) of grey needles, non-melting at 330° C.

| Analysis: $C_{16}H_{13}N_3O \frac{1}{2} H_2O$: 272.3 | C | H | N |
|---|---|---|---|
| % calculated | 70.57 | 5.18 | 15.43 |
| % found | 70.63 | 5.32 | 15.22 |

EXAMPLE 13

This example illustrates the proceeding (b) for obtaining the compound of formula (12) in which $R'_2$ is hydrogen, i.e. the compound of formula (12a) hereinafter,

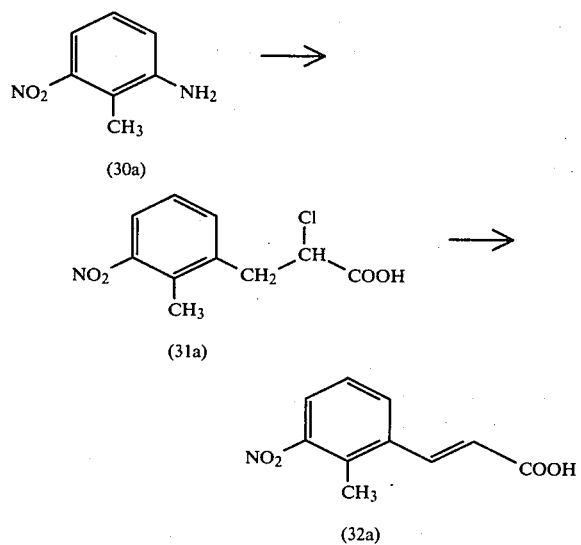

2-methyl-3-nitro-trans cinnamic acid (32a)

In a 1 liter, 3-necked flask were introduced 15.2g of 2-methyl-3-nitro aniline (30a) which were dissolved in 200 ml of acetone and 17 ml of concentrated hydrochloric acid were added, then the whole was cooled to 0° C.

By maintaining the solution below 5° C., and with stirring, diazotisation was effected by progressively adding a solution of 7.5g of sodium nitrite in 25 ml of water.

After having left the preceding solution with stirring for 30 minutes, it was poured slowly into a 3-necked flask containing a mixture consisting of 100 ml of acrylic acid, 7.6g of cupric chloride dissolved in 25 ml of water and 100 ml of acetone, the whole being maintained at a temperature of 35° C. for the whole duration of the addition which lasts from 15 to 25 minutes.

This new mixture was maintained with stirring at 35° C. for one hour than the acetone and the excess of acrylic acid were evaporated. The residue was taken up with chloroform, washed in water and the chloroform phase was exhausted with a cold 2N sodium hydroxide solution (twice 50 ml). By acidification with hydrochloric acid, the (2-methyl-3-nitro-phenyl)-chloro-propionic acid (31a) was precipitated, filtered off and dried.

The latter was entirely treated by heating it with reflux for 30 minutes in 100 ml of methanol containing 10 g of potassium hydroxide and, after evaporation, the residue was taken up with water and acidified in the cold by hydrochloric acid. The precipitate was filtered, dried and recrystallised from xylene to give 2-methyl-3-nitro-cinnamic acid (32c), melting point 222° C.

Yield (with respect to the amine used):11.9g (57.5%).

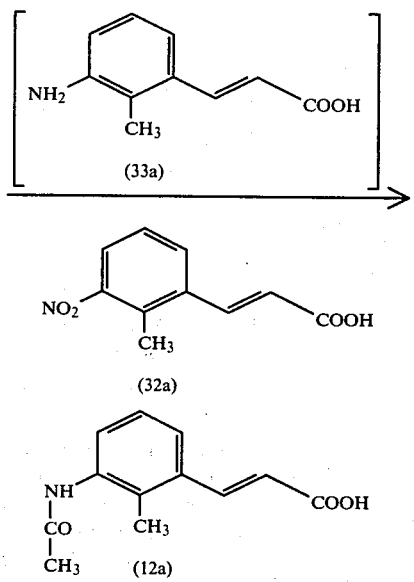

2-methyl-3-acetylamino-trans cinnamic acid (12a)

In a 2-litre 3-necked flask, 84.5g of nitro-acid (32a) were dissolved in 750 ml of acetic acid, 100g of commercially available Raney nickel washed with acetic acid and hydrogen were added, stirring being effected under a hydrogen atmosphere at normal pressure and at ambient temperature.

Hydrogenation was stopped when the volume of hydrogen consumed exceeded the theoretical volume (28.4 l instead of the necessary 27.4) or after 4 hours 25 minutes stirring.

The catalyst was filtered off, was washed with acetic acid and half of the solvent was evaporated. 90 ml of acetic anhydride were then added and the mixture was heated with reflux for 1½ hours then evaporated to dryness.

The residue was taken up with 500 ml of boiling acetic acid, filtering was carried out in the hot to eliminate the insoluble Ni salts and, on cooling, 44 g of the expected acid were obtained.

By concentration of the mother liquors, about 10 g of the desired compound (12a) were further recovered, melting point 265°–267° C. The total yield was a minimum of 54g (60.2%).

PHARMACOLOGICAL TESTS

The following tests were made in groups of 10 mice, unless stipulated to the contrary.

Test 1: Study of the antitumoral properties of the compounds of the invention of L 1210 leukemia The antitumoral properties of the compounds according to the invention were determined by their curative action on test inoculated L 1210 leukemia.

This leukemia was maintained on CBD 1(C 57 B 16×DBA/2) Fl mice. The compounds to be tested were injected by the IP route one or more days after the inoculation of the cells (single injection). The results obtained, shown in table I hereinafter, are expressed in percentage of increase of life span (ILS %) and in percentage of the number of cells killed by the compound to be tested, the survival of the animals being proportional to the number of cells injected.

The percentage of the like span ILS % (Cancer. Res. 1971, 31, 1883–1887) is the following ratio:

$$ILS \% = \frac{S^t - S^c}{S^c} \times 100;$$

$S^t$ = survival of the treated animals
$S^c$ = survival of the control animals

The results of table I show that the products according to the invention possess antitumoral properties.

Test 2: Viro-induced Leukemia: Friend leukemia

The protective power of the compounds according to the invention was sought on Friend leukemia, inoculated into DBA2 mice aged from 5–6 weeks. The viral inoculum was produced from a homogenate of leukemic spleen (p/volume) diluted to 1/250 in isotonic phosphate buffer without $Ca^{++}$ nor $Mg^{++}$ (PBS), corresponding to 100 SD 50 (i.e. to the dose of virus which induces a splenomegaly in 50% of the inoculated mice).

The virus was injected by the IP route and in a volume of 0.2 in ml. The product to be tested was injected 5 hours after the virus or 1 day after the virus at the dose indicated in a volume of 0.1 ml (IP route). Each group of twenty control mice received the virus and a placebo or the product to be tested, 10 mice were sacrificed on the 21st day, and their spleen removed and weighted. The mice were considered as leukemic when the weight of their spleen exceed 200 mg. For the 10 mice, the life span of the animals was determined.

The results obtained are shown in table II. These results show that these products possess an antiviral activity in addition to their antitumoral activity.

Test 3: Study of the development of the viro-induced Moloney sarcoma

The injection of Moloney virus [C. Jasmin et al. J. Nat. Cancer Inst. 1974 53 469–474] by the intramuscular i.m.route into new-born mice led after 10 days to the formation of a sarcoma. The appearance of the tumour was proportional to the dose of virus injected. The viral inoculum was constituted by a tumour homogenate diluted to 1/250, this corresponding to 10 TID 50, i.e. to the dose of virus inducing the appearance of a tumour in 50% of the animals infected. At this dose, 80 to 100% of the animals developed a tumour, and 100% of the survivors became leukemic. The experiment thus consisted in noting the number of mice presenting tumours, the regression, or not, of these tumours and finally in sacrificing the surviving animals after 2 months and in noting the presence or absence of splenomegaly (evidence of a leukemia). The virus was inoculated into new-born mice of 3 to 5 days by the IM route, and the mice received the following day (J+1) or five hours after injection (JO+5 hours) the product to be tested by the IP route. The results obtained are as follows:

Controls virus:
  80% of the young mice presented tumours
  10% of the tumours regressed
  30% of the animals survived and all presented a leukemia.
Compound of example 7:injection on J+1; 1 μg/mouse (0.5mg/kg)
  70% of the mice presented tumours
  90% of the tumours regressed
  90% of the animals survived
  0% presented a leukemia.
HUM : injection on J+1; 5 μg/mouse (2.5 mg/kg)
  20% of the animals present a tumour
  100% regression
  10% of the mice were leukemic.
HUM: injection on J+1, 1 μg/mouse (0.5 mg/kg)
  30% of the animals present a tumour
  90% regression
  90% survivors
  33% were leukemic.
Controls virus:
  90% of the animals present a tumour
  40% of the tumours regressed
  90% of the mice survived
  45% of the mice were leukemic.
Compound of example 7: injection on JO+5 hours; 1 μg/mouse (0.5 mg/kg).
  5% of the animals present a tumour
  100% regressed
  100% survived
  40% present a leukemia.
Compound of example 1: injection on JO+5 hours; 1μg/mouse (0.5 mg/kg)
  50% of the animals present a tumour
  30% regressed
  75% survived
  65% are leukemic. Test 4: Investigation of the toxicity The toxic dose has been sought, on adult (C 57,BL 6×DBA/2) Fl mice and on new-born mice, of the compounds of the invention by injection by injection by the IP route. The results obtained are given hereinafter:

1- On adult Fl mice (C 57 BL 6×DBA/2)Fl (IP route)

(a) Compound of example 1:
  Injectioni of
  2 mg/mouse (80 mg/kg)=5 dead /6
  1 mg/mouse (40 mg/kg)=1 dead/8
  9.5 mg/mouse (20 mg/kg)=1 dead/6
(b) Compound of example 7:
  Injection of
  1 mg/mouse (50 mg/kg)=1 dead/3
  0.6 mg/mouse (30 mg/kg)=5 dead/10
  0.5 mg/mouse (25 mg/kg) 0 dead/5
  0.3 mg/mouse (15 mg/kg)=0 dead/6
The $LD_{50}$ of the compound of example 7 is therefore 30 mg/kg.

2-On new-born mice (IP route)

5 μg: 2.5 mg/kg=3 dead/8, mice puny in appearance
HUM 10 μg: 5 mg/kg=3 dead/8, mice puny in appearance.

These results show that the toxic dose of the compound of example 7 is higher than 2.5 mg/kg of mouse.

Test 5- Cytotoxic effect in vitro

The cytotoxic efforts of the compounds according to the invention were tested in vitro on cultures of hamster, human and mouse cells.

In particular, the BHK21 strain of hamster cells and a clone derived from this strain transformed by Hamster Sarcoma Virus (HS5 clone) were used.

After detachment by trypsine, the cells were seeded in plastic Petri dishes (35 mm diameter) at the concentration of $2.10^5$ cells/dish, in Eagle medium supplemented with "Bactotryptophosphate" Broth, Difco and 10% calf serum (R. M. STOKER and I. MACPHERSON Virology 14, 1961, 359).

5 hours later, the cells were well attached to the plastic support, and the products to be tested were added, dilutions having been made thereof in water or in DMSO (dimethylsulfoxide) if the product is sparingly soluble in water. In this latter case, a control was made with the same final concentration of DMSO in the culture medium.

The state of the cells was examined 24, 48 and 72 hours afterwards.

The results (table III) clearly show that the products are clearly cytotoxic at concentrations from 0.2 to 10 μm, and that the most active product, i.e. the compound of example 7, is ust as active as the already known derivatives, 2-methyl-9-hydroxy-ellipticinium acetate and 9-hydroxy-ellipticine.

The effects on the two types of cells, normal and transformed, are similar.

Test 6: Action on the macromolecular syntheses

The action of the compounds according to the invention was studied by the incorporation of precursors marked by radioactive isotopes:
$^{14}C$ methyl-thymidine for studying the DNA synthesis
$^3H5$ for that of the RNA
$^3Hv$ valine for that of the proteins.

These precursors were given for a period of 30 minutes at varying times after the addition of the product to be tested.

The incorporation is measured after lysis of the cells for 1% of sodium dodecylsulfate and precipitation by 5% of trichloroacetic acid. The acidosoluble precipitate was collected on glass fibre Whatman GF/A filters. The filters were dried and counted in a liquid scintillation spectrometre.

Table IV gives the typical results for the compound of example 1: 5,11-dimethyl-dipyrido-[4,3-b][3,4-f]indole.

It is ascertained that this compound reduces very rapidly, in the hours following its addition, the DNA and RNA syntheses and, to a lesser degree, the synthesis of the proteins.

Experiments made on synchronised cells (G. TORFIER, J. GRUEST & L. MONTAGNIER Experimental Cell Research 85, 1974, 437) have shown that the compound of example 1 stops, in the first minutes following its addition, the replication of the DNA, both at its initiation and elongation steps.

Test 7: Study of the antitumoral activity in vitro

This activity was measured on a tumoral strain derived from the murine leukemia due to the C. FRIEND virus.

The tumoral cells multiply in suspension in a "RPMI 1640" medium (Catalogue of GIBCO Bio-cult. Ltd, Washington Road, Sandyford Industrial Estate, PAISLEY PA 3 4EP, Renfrewshire, Scotland) supplemented with 20% of embryonary calf serum, penicillin and streptomycine. The duplication time of these cells is 11 hours. The growth fraction is equal to 1 or very close to 1 (all the cells are in the cycle). The cultures are sub-cultured at time $t=0$ at the concentration of $2.10^5$ cells per ml in Falcon dishes containing 4 ml of medium. After twenty four hours, the product to be tested was added, i.e. at a moment when the cultures are in exponential phase of growth. Twenty four hours after the addition of the product, the cells are counted and the precentages of living cells determined by an exclusion test using "trypan" blue. Two dises may therefore be defined:

(1) LD 50
(2) LD 100

| | LD 100 | LD 50 | Activity*: $\frac{LD\ 50\ HUM}{LD\ 50\ X}$ |
|---|---|---|---|
| Reference product: 9-hydroxy-ellipticinium acetomethylate | $7\ 10^{-7}$ | $3\ 10^{-7}$ | 1 |
| compound of example 1 | $5\ 10^{-7}$ | $10^{-7}$ | 3 |
| compound of example 2 | $5\ 10^{-6}$ | $1.5\ 10^{-6}$ | 0.2 |
| compound of example 5 | $6\ 10^{-6}$ | $2\ 10^{-6}$ | 0.15 |
| compound of example 6 | $5\ 10^{-6}$ | $10^{-6}$ | 0.3 |
| compound of example 7 | $5\ 10^{-8}$ | $10^{-8}$ | 20 |

*Activity: This figure (ratio of the $LD_{50}$ of HUM with respect to the $LD_{50}$ of the product lobe tested) is quite arbitrary and gives an idea of the activities of the different products by comparing them with the HUM, the most active product in the series of the ellipticines.

Test 8: Acute toxicity in vivo

The products to be tested were injected by the IP route into groups of 10 mice at various dilutions. Each day, the number of dead animals is noted. If the doses are well chosen, a 100% lethal dose and a 50% lethal dose have been able to defined for each product. This study is limited to two months. Two isogenic mouse strains were systematically used: C3H/He and ICFW.

| | Mouse strain | LD 100 | LD 50 |
|---|---|---|---|
| Compound of example 1 | C3H | 200 mg/kg | 100 mg/kg |
| | ICFW | 200 mg/kg | 150 mg/kg |
| compound of example 7 | C3H | 35 mg/kg | 20 mg/kg |
| | ICFW | 25 mg/kg | 15 mg/kg |

Test 9: Action on chloromonocytary tumoral cells

In this test, the action of the products according to the invention on chloromonocytary tumoral cells was determined according to the chloroleukemia of the mouse test (ICFW mouse, co-sanguine CFW strain) isolated in Unit 22 (B. TAMBOURIN and F. WENDLING) of the "Institut National de la Santé et de la Recherche Médicale—Paris" (I.N.S.E.R.M.) in a mouse injected with a variant of the Friend virus.

The tumour kills all the animals injected in $19.3\pm 2$ days. This tumour develops in semi-solid ascitic form; the peritoneum is invaded, both by solid tumoral masses and cells in suspension in the ascitic liquid. The tumour is transmitted by the cells of the suspension which produce the tumoral masses and the ascitic cells.

|  | Mean survival time without treatment | Mean survival time after treatment |
|---|---|---|
| Compound of formula 8 (40 mg/kg 6 hours after inoculation) | 18.5 ± 2 days | 25.3 ± 3.1 days |
| Compound 21 (1 mg/kg 24 hours after inoculation) | 18.9 ± 1.8 day | 29.0 ± 3.0 days |

Test 10- Comparison of the antitumoral activity of the compound according to example 7 with that of known products The compound of example 7, i.e. 1-(γ-diethylaminopropyl)amino-5-methyl-dipyrido-[4,3-b][3,4-f] indole or known compounds were injected into L 1210 leukemic mice 1 or 3 days after the inoculation of the cells at the doses indicated in tables V to VII and the mean survival time (MST) and the percentage of increased life span (ILS %) were measured.

Indications concerning the known products used in this example and particularly their antitumoral properties, their secondary effects and their use in man may be found in "La Chimiothérapie des Cancers", by G. MATHE and M. KENIS Expansion Scientifique Francaise, 3rd edition, Paris 1975.

Test 11

L 1210 leukemic mice were injected with the compound of example 8 (compound 22), i.e. 1-(γ-dimethylaminopropyl)amino-5-methyl-dipyrido [4,3-b][3,4-f] indole, one day after the inoculation of the cells (day J + 1) at the doses indicated in table VIII and the mean survival time (MST) and the increase in life span (ILS %) were measured.

This test was carried out with $10^3$, $10^4$ and $10^5$ leukemic cells on day J. This test was also carried out with the compound of example 7, i.e. 1-[(γ-diethylaminopropyl)amino]-5-methyl-dipyrido [4,3-b][3,4-f] indole (compound 21).

The results obtained are indicated in table VIII. This table also shows the number of the surviving mice; a mouse is considered as survivor if it has survived at least 2 to 3 months after the inoculation of the leukemic cells.

Test 12- Study of the protection of the leukemic mice inoculated L 1210 cells) by a single dose or a fractioned dose.

The compound of example 7, i.e. 1-[(γ-diethylaminopropyl)amino]-5-methyl-dipyrido [4,3-b][3,4-f] indole was injected into L 1210 leukemic mice by one injection (10 mg/kg at day J + 3) or by fractioned doses (2.5 mg/kg each injection on days J + 3, J + 4, J + 5 and J + 6).

The results in table IX show that a single dose has greater antitumoral activity than the same dose injected on 4 occasions.

Test 13- Lewis carcinoma

For this test, reference may be made to the following works:

"carcinome pulmonaire de Lewis" (3LL), K. SUGIURA and C. C. STOCK", Cancer Res. 1955 15 38-51.

La Chimiothérapie des cancers by G. MATHE and Y. KENIS, Expansion Scientifique Française, 3rd edition, Paris 1975. S. A. SCHEPARTZ Screening, 1971, Cancer Chemiother. Rep. Part 3 vol. 2, page 3.

In this test, cells ($10^6$ cells) removed from a tumour-carrying mouse were injected into mice ($BDF_1$) by the IM route. The mice developed, 10 to 15 days after the inoculation, a tumour at the spot where the injection was made. On the other hand, these cells made metastasis in the lung, forming colonies on the pulmonary surface. The antitumoral and antimetastasic effect of a product may therefore be judged on mice thus treated.

Investigation of the antimetastasic effect of the compounds of examples 7 and 8 of the invention $10^6$ cells taken from a tumour-carrying mouse were injected by the IM route (left-hand paw) into groups of 10 mice and the compounds to be tested were inoculated by the IP route on day J + 5 by single or fractioned injection. The mean survival time (MST) and the increased life span (ILS %) were determined.

|  | Number of injections | MST | ILS |
|---|---|---|---|
| non-treated controls |  | 25 |  |
| Mice treated with the compound of example 7 | 4 injections J + 5 + 6 + 10 + 11 2.5 mg/kg each | 27.4 | 9.6 |
| Mice treated with the compound of example 7 | 1 injection J + 5 10 mg/kg | 32.7 | 30.8 |
| Mice treated with the compound of example 8 | J + 5 5 mg/kg | 27.44 | 9.8 |

It may be concluded that the compounds of examples 7 and 8 give a protective action concerning the metastasic pulmonary invasion of the lung. In fact, one treated mouse and one non-treated mouse were sacrified on day J + 22 and the pulmonary metastases counted: 77 metastases were counted in the non-treated mouse and 35 in the mouse treated on day J + 5 (one injection) with the compound of example 7.

Test 14: viro-induced leukemia: Friend leukemia (A) As in test 2 hereinabove, the Friend leukemia virus inoculum was obtained from leukemia spleen and diluted to contain 100 $SD_{50}/0.2$ ml ($SD_{50}$=spleen enlarging dose 50 percent). The product to be tested was compound 21 (obtained according to example 7). It was given by I. P. route as a single injection 1 day after virus inoculation.

The results obtained are indicated in table Xa. Treatment with this compound 21 as well as with compound of example 1 (see table II) resulted in a significant increase of the life span.

Half of the mice treated with compound of example 1 according to test 2 or with compound 21 as above explained were sacrificed 21 days after virus incoulation, their spleen removed and weighted. The mean spleen weight for the control mice was 2,520 mg (1,919–2,866), that of mice treated with 5 mg/kg of compound of example 1 was 2,013 mg (887–2,793), with 25 mg/kg 1,803 (718–2,635) and with 50 mg/kg 960 (373–1,230). For mice inoculated with compound 21 1 day after the virus, the mean spleen weight was 1,935 mg (500–2,950). The decrease of the splenomegaly is in line with the increase of the life span and suggests that the compounds act also as antiviral agents in this system.

TABLE Xa

Action of compound 21 on Friend leukemia

| | Drug (mg/kg) | Range of death (in days) | MST | ILS % |
|---|---|---|---|---|
| Control mice | 0 | 20–56 | 32 | |
| mice treated with compound 21 (ex.7) | 5 | 27–52 | 44.5 | 39 |

(B). The proceeding of test 2 was repeated by using the compound 21 i.e. 1-[(γ-diethylaminopropyl)amino]-5-methyl-dipyrido [4,3-b][3,4-f] indole obtained according to example 7.

This test was carried out with a single dose of compound 21 (20 mg/kg) and with various virus doses. The results obtained are shown in table Xb.

TABLE Xb

Viro induced leukemia: Friend leukemia
Compound 21: single dosage: 20 mg/kg
various dosages of virus

| | Range of death[1] | MST[2] | ILS %[3] | Survivors 4 months after inoculation |
|---|---|---|---|---|
| Controls virus 1/500 (1000 SD$_{50}$) | 24–38 | 29.1 | — | 0 |
| Compound 21 J + 1 | 31–51 | 40.7 | 40 | 0 |
| Controls virus 1/2000 (250 SD$_{50}$) | 25–44 | 33.8 | — | 0 |
| Compound 21 J + 1 | 50–82 | 55.4 | 64 | 2 |
| Controls (virus 1/1000) | 18–36 | 24.3 | — | 0 |
| Compound 21 J + 1 | 30–54 | 44.4 | 82.7 | 0 |

[1]Range of death: the first figure indicates the date when the first mice died and the second the date when the latter mice died
[2]MST: Mean of survival time
[3]ILS % (increased life span) = increase of the life time; it takes care of dead animals $$\frac{MST_t - MST_c}{MST_c} \times 100$$

$MST_t$ = treated animals; $MST_c$ = control animals

Test 15: L 1210 Leukemia

The proceeding of test 1 was repeated with the compound of formula 8 obtained according to example 1, i.e. 5,11-dimethyl-dipyrido [4,3-b][3,4-f]indole. In this test, the compound of formula 8 was injected four days after the inoculation of the cells (50 mg/kg). The results are shown in table XI wherein the results obtained with the same compound injected one day after the cell inoculation are also reported (see experiment n° 2 in table I). The results show that the increased life span (ILS %) was higher when the product was given earlier after the cells inoculum.

TABLE XI

| | Cell number | Drug | Dose mg/kg | Day of inoculation* | Range of death | MST (day) | ILS % |
|---|---|---|---|---|---|---|---|
| Exp.=2 | 10$^6$ | 0 | 0 | 0 | 7–12 | 7.8 | |
| | 10$^6$ | compound of example 1 | 50 | +1 | 9–15 | 11.5 | 47.3 |
| | 10$^5$ | 0 | 0 | 0 | 8–11 | 9.3 | |
| | 10$^5$ | compound of example 1 | 50 | +1 | 10–13 | 12.85 | 38.1 |
| | 10$^4$ | 0 | 0 | 0 | 10–13 | 11 | |
| | 10$^4$ | compound of example 1 | 50 | +1 | 11–14 | 12.3 | 11.8 |
| Exp=4 | 10$^6$ | 0 | 0 | 0 | 6–7 | 6.7 | |
| | 10$^6$ | compound of example 1 | 50 | +4 | 8–13 | 9 | 34.3 |
| | 10$^5$ | 0 | | 0 | 8–12 | 8.9 | |
| | 10$^5$ | compound of example 1 | 50 | +4 | 10–11 | 10.3 | 15.7 |
| | 10$^4$ | 0 | 0 | 0 | 10–11 | 10.5 | |
| | 10$^4$ | compound of example 1 | 50 | +4 | 10–16 | 12 | 14.7 |

*The drug is administered 1 day (+1) or 4 days after the cells inoculum. Compound of example 1 = dimethyl-5,11 dipyrido [4,3-b] [3,4-f] indole.

Test 16: Relationship between structure and activity of various dipyrido indoles differing by the R'1 substitution.

The R'1 substitution at the 1 position seems to be very important for the protective effect of the derivatives against L1210 tumor cell growth.

L1210 leukemia has been maintained by weekly passages on (C57B16×DBA/2)F1 mice. On day 0, mice were inoculated by I. P. route with various numbers of L1210 ascitic tumor cells in volumes of 0.1 ml. Subsequently as indicated, drugs were administered in Ca++ and Mg++ free PBS solutions (Gibco) or in Mac Coy's medium (Gibco or Microbiological Associates).

The relationship between the size of leukemic cell inoculum given IP and the host life span was determined in groups of 10 mice after inoculation of 10$^3$ to 10$^6$ cells in 0.1 ml of Mac Coy's medium. The decrease in the average of host life-span between each consecutive ten-fold increase in size of the leukemic cell inoculum was 2 days. According to the method of calculation of Dombernowsky, the doubling time was 0.615 days.

If the R'1 substituting lateral chain is γ-diethylaminopropyl (compound 21) or γ-dimethylaminopropyl (compound 22), these compounds have similar or higher antitumoral activity. As shown in table XII (compound 21) and (compound 22) compete favorably with Ellipticinium acetate (HUM) indicating that the pyrido-indole structure is more effective than the pyrido-carbazole nucleus (ellipticine).

TABLE XII

| Cell number | Drug | Dose mg/kg | Day of inoculation | Range of death | MST | ILS % | 60 day surv. |
|---|---|---|---|---|---|---|---|
| $10^4$ | 0 | 0 | 0 | 10–14 | 11.8 | — | 0 |
| $10^4$ | compound 21 | 5 | +1 | 13–21 | 16.2 | 33.3 | 1 |
| $10^4$ | compound 21 | 0.5 | +1 | 11–15 | 13.54 | 11.5 | 0 |
| $10^4$ | HUM | 5 | +1 | 14–20 | 14.9 | 22.6 | |
| $10^3$ | 0 | 0 | 0 | 13–16 | 13.8 | — | 0 |
| $10^3$ | compound 21 | 5 | +1 | 15–22 | 17 | 23.2 | 5 |
| $10^3$ | compound 21 | 0.5 | +1 | 14–20 | 16.2 | 17.4 | 3 |
| $10^3$ | HUM | 5 | +1 | 14–20 | 16.86 | 22.15 | 3 |
| $10^4$ | 0 | 0 | 0 | 10–12 | 10.9 | | 0 |
| $10^4$ | compound 21 | 5 | +1 | 14–21 | 18 | 65.1 | 1 |
| $10^4$ | compound 22 | 5 | +1 | 12–15 | 13.7 | 25.7 | 3 |
| $10^4$ | compound 22 | 2.5 | +1 | 10–19 | 14.7 | 34.9 | 1 |
| $10^5$ | 0 | 0 | 0 | 8–14 | 9.05 | | |
| $10^5$ | compound 22 | 5 | +1 | 11–16 | 13.8 | 52.5 | 0 |
| $10^4$ | 0 | 0 | 0 | 10–13 | 11.2 | | |
| $10^4$ | compound of the example 2 | 20 | +4 | 10–17 | 11.3 | 0.9 | 0 |

Test 17: Relationship between the length of the substituting chain and the activity.

The importance of the substitution of R'1 on 1 position for the antitumoral activity of these compounds was demonstrated above. If one varies the length of the lateral chain γ-diethylaminopropyl-amino 1 for the compound 21 or γ-diethylamino-ethylamino 1 for compound 23, as shown in table XIII, both compounds are active against L1210 leukemia at the same dosage. However compound 21 is less toxic (50 mg/kg for compound 21 and 25 mg/kg for compound 23), it has a higher ILS% than compound 23 and 1 mouse survived up to 60 days. These results indicate that the diethylaminopropylamino-1 substitution corresponds to the best length of chain for the therapeutic action of the derivative. Increasing the lateral chain by (γ-methyl δ-diethylamino-butyl)amino 1 such as compound 24, similar antitumoral effect is found, conforming that compound 21 is the compound the most active on the mice.

TABLE XIII

| | Day of inoculation | Range of death | MST | ILS % | Survivors up to 60 days |
|---|---|---|---|---|---|
| Control | | 8–9 | 8.8 | | |
| Compound 21 | +1 | 12–18 | 14.9 | 69.2 | 1 |
| Compound 23 | +1 | 11–18 | 14.6 | 65.2 | 0 |
| Control | | 10–13 | 11.2 | | |
| Compound 21 | +4 | 14–32 | 18.5 | 65.6 | 0 |
| Compound 24 | +4 | 12–20 | 17.5 | 56.25 | 0 |

Test 18: Relationship between dose and L1210 antitumoral activity of compound 21

The dose response of the activity of compound 21 as shown with L1210 leukemia according to test 1 is as follows:

At 5 mg/kg, the mean survival time (MST) is significantly increased (ILS=87 percent); at higher doses of compound 21, the MST is always significant increased (ILS=52 p.cent at 10 mg and 75 p.cent at 20 mg/kg) and some were surviving up to 60 days (10 p.cent of inoculated mice at 10 mg and 20 p.cent at 20 mg per kg).

Test 19: Effect of the time of administration of compound 21

As shown in table XIV, a single injection of compound 21 increased significantly the mean survival time when given as later as 6 days after the L1210 cells inoculation. The results confirm that compound 21 is more effective when given earlier after the cells inoculation (ILS=56.4% at day + 2, 43% at day + 3 instead of 20.8% at day + 6 or 2% at day + 7). The non-protective effect at day + 7 could be explained by the fact that some cells migrate through a compartment inaccessible to the drug (as postulated by J. B. Le Pecq for the 9-hydroxy-ellipticine).

TABLE XIV

| Day of administration ** | Range of death | MST | ILS % | Estimated number of cells*** |
|---|---|---|---|---|
| Control | 10–11 | 10.1 | | |
| BD 40* +2 | 15–17 | 15.8 | 56.4 | $10^5$ |
| +3 | 12–17 | 14.4 | 43.0 | $5.10^5$ |
| +4 | 10–14 | 12.4 | 22.8 | $10^6$ |
| +5 | 10–13 | 11.9 | 17.8 | $5.10^6$ |
| +6 | 10–14 | 12.2 | 20.8 | $10^7$ |
| +7 | 10–13 | 10.3 | 2.0 | $5.10^7$ |

*BD 40 is given I.P. at 0.1 ml containing 0.4 mg/mice (20 mg/kg)
**Day 0 is the day of inoculation of $10^4$ L1210 cells given I.P.
***Evaluation of the number of leukemic cells by the mean of calculation of the doubling time (according to P. Dombernowsky).

Test 20: Study of the combination of compound 21 with other drugs

An increase of protection of mice inoculated with Lewis lung carcinoma 14 days before a low priming dose followed by a high challenge dose of endoxan was reported by J. Millar 1978, tenth congress of chimiotherapy (1978) in press., G. A. Preasant Cancer vol. 40 1977 p. 987–993 for the therapy of drug-resistant breast carcinoma used a combination of endoxan, BCNU and Adriamycin the following day.

The results concerning similar experiments (breast carcinoma and Lewis carcinoma) with compound 21 are discussed in table XV. A priming dose of endoxan (100 mg/kg) was given 3 days after $10^5$ leukemic cells (20 mice). The following day, 10 mice received 0.1 ml of PBS (control mice) and 10 mice received 20 mg/kg of compound 21. Increase in life span was significantly higher in mice receiving endoxan and compound 21 compared to the mice with endoxan or compound 21 alone. The results listed in table XV suggested that compound 21 given one day after endoxan or endoxan-BCNU gave rise to a higher protection of mice than endoxan, endoxan + BCNU or compound 21 given alone. Taking as control mice the endoxan treated mice, the ILS% is 57 for endoxan + compound 21 treated mice and 63 for endoxan + BCNU + compound 21 treated mice.

TABLE XV

| | Range of death | MST | ILS % |
|---|---|---|---|
| Control | 10–13 | 11.2 | — |
| Endoxan | 11–17 | 13.1 | 16.9 |
| BD 40 | 14–32 | 18.5 | 65.2 |
| Endoxan BD 40 | 18–24 | 20.6 | 84 |

TABLE XV-continued

|  | Range of death | MST | ILS % |
|---|---|---|---|
| Endoxan + BCNU | 10-17 | 13.7 | 22.3 |
| Endoxan + BCNU + BD 40 | 18-24 | 21.4 | 91 |

BD 40 is given I. P. at day + 4 (20 mg/kg)
Endoxan is inoculated I.P. at day + 3 (100 mg/kg) and BCNU immediately after endoxan (2 mg/kg).
Day 0 is the day of inoculation of $10^5$ cells given I.P.

mice under a volume of 0.1 ml I.P. after dilution in Mac Coy's medium.

The toxicity of the drugs after intraperitoneal injection was estimated from the mortality rate up to the 30th day. The minimal quantity resulting in 100% deaths was 50 mg/kg for compound 24, 50 mg/kg for compound 21 and for compound 22, 25 for compound 23. In general, the deaths occured early after drug administration (4-6 days for compound 24, 4-8 for compound 21, 3-5 for compound 22 and 4-6 for compound 23).

TABLE I

Study of the antitumoral properties of the compounds according to the invention on L 1210 leukemia

| Compound tested | Experiment | Number of cells injected | Quantity in mg/mouse (mg/kg) | ILS % | Number of cells found | Number of cells killed | Surviving mice |
|---|---|---|---|---|---|---|---|
| Compound of example 1 (formula 8) | experiment n° 1 J + 2** | $10^6$ $10^5$ $10^4$ $10^3$ | 1 mg/mouse (50mg/kg) | 34,32 15,73 14,78 3 | $10^5$ 40,000 6,000 800 | 90% 60% 40% 20% | 0 0 1/10 |
| Compound of example 1 (formula 8) | experiment n° 2 J + 1** | $10^6$ $10^5$ $10^4$ | 1 mg/mouse (50 mg/kg) | 47,3 38,1 11,8 | 8000 2000 5000 | 99% 98% 50% |  |
| Compound of example 1 (formula 8) | experiment n° 3 |  | 0,1 mg/mouse 0,05 mg/mouse | no significant difference with the controls $10^4$ cells $10^3$ cells |  |  |  |
| Compound 20 (example 6) |  |  | 0,1 mg/mouse | 0,1 mg toxic and no difference with the controls $10^4$ cells $10^3$ cells |  |  |  |
| Compound 21 (example 7) | Product injected by I.P. route J + 1** | $10^4$ $10^3$ | 0.1 mg/mouse (0.5 mg/kg) 0.1 mg/mouse (5 mg/kg) 0.01 mg/mouse (0.5 mg/kg) 0.1 mg/mouse (5 mg/kg) | 33.3 11.5 17.4 23.2 | 60 $10^3$ 80 40 | 99.94 90 92 96 | 1/10 5/10 |
| HUM* |  |  | 0.1 mg/mouse (5 mg/kg) |  |  |  |  |
|  | product injected by I.P. route J + 1** | $10^4$ $10^3$ | 0.1 mg.m (5 mg/kg) 0.1 mg (5 mg/kg) | 22.6 22.15 | 400 60 | 96 94 | 1/10 3/10 |

*HUM: 2-N-methyl-9-hydroxy-ellipticinium acetate
**J + 1 or J + 2: injection one or two days after inoculation f the cells.

Test 21 : Toxicity of compounds 21,22,23, and 24.

All drugs were dissolved in aqueous solutions adjusted at pH 5 with acetic acid and inoculated to the

TABLE II

| Mouse | Virus | Viro-induced leukemia - Friend leukemia | | | |
|---|---|---|---|---|---|
|  |  | Product to be tested | Mean survival time** Days | ***ILS % | Weight of the spleens on the 21st day in mg |
| control | *VFA 1/250 (1) | — | 31.7 (26-47) |  | 2519 mg |
|  | VFA 1/250 (2) | — | 28 (14-17) |  | (2866-1919) |
| Treated | VFA 1/250 | compound of example 1 (formula 8) 5hrs after the virus |  |  |  |
|  |  | 0.1 | 47.6 (26-78) | 59.5 | 2013 mg (887-2793) |
|  |  | 0.5 | 34.2 (22.54) | 14.6 | (1803 mg) (718-2635) |
|  |  | 1 mg | 41.7 (14-81) | 39.7 | 959,6 mg (373-1230) |

Male DBAZ mice aged 5-6 weeks
Experiment of 4.8.76:
*VFA: anaemic Friend virus injected by the I.P. route, 0,2 ml dilution 1/250 - 100 SD 50
**Mean survival time between brackets, dates on which the first and last mouse died
***Increase in the life span per 100

TABLE III

Minimum dose involving complete inhibition of growth

| Cells | Compound example 1 | Compound example 2 | Compound example 5 | Compound example 6 | Compound example 7 | HE* |
|---|---|---|---|---|---|---|
| C13/8 | 0.5 M | 2 | 5 | 2 | 0.25 | 0.25 |
| HS 5  | 0.5 M | 2 | 5 | 2 | 0.25 | 0.25 |

*HE = 9-OH-hydroxy-ellipticine or 2-acetomethylate-9-hydroxy-ellipticinium

TABLE IV

Inhibition of the macromolecular syntheses by the compound of example 1

| Time, in hours, of marking after addition of the product | Incorporation in the DNA (in % of the non-treated control) | Incorporation in the RNA (in % of the non treated control) | Incorporation in proteins (in % of the non treated control |
|---|---|---|---|
| 0.5 | 41  | 33  | 40 |
| 3   | 14  | 13  | 37 |
| 6   | 6.3 | 3.7 | 16 |
| 9   | 6   | 9   | 17 |
| 24  | 4   | 31  | 17 | the concentration of the product is 5 M the cells HS5 were seeded 24 hours beforehand at a concentration of $5.10^5$ per Petri dish of 60 mm.

TABLE V

| Compound tested | Injection | Quantity per mouse | Range of death | MTS | ILS % |
|---|---|---|---|---|---|
| Control $10^4$ cells | | | 10-15 days | 11 | |
| Compound of example 7 | J + 1 | 0.2 mg | 6-1 mouse alive on 30th day | | |
| Compound of example 7 | J + 3 | 0.2 mg | 11-17 | 13.8 | 25.45 |
| Thiotepa | J + 3 | 0.1 mg | 10-11 | 11 | 0 |
| Mitomycine | J + 3 | 0.016 mg | 10-15 | 11.54 | 4.95 |
| BCNU | J + 3 | 0.1 mg | 10-12 | 11.1 | 0.9 |
| Methotrexate | J + 3 | 0.250 mg | 15-17 | 15.9 | 44.62 |
| Endoxan | J + 3 | 4 mg | 13-3 mice alive on 30th day/10 | | |

TABLE VI

| | Quantity in mg/mouse | Injection | Range of death | MTS | ILS % |
|---|---|---|---|---|---|
| Control $10^5$ cells | | | 9-10 | 9.06 | |
| Thiotepa | 0.1 mg | J + 3 | 9-10 | 9.2 | 1.54 |
| Mitomycine C | 0.016 mg | J + 3 | 9-10 | 9.06 | 0 |
| BCNU | 0.1 mg | J + 3 | 8-9 | 8.8 | 0 |
| Methotrexate | 0.250 mg | J + 3 | 12-14 | 12.62 | 39.35 |
| Compound of example 7 | 0.2 mg | J + 1 | 9-16 | 12.6 | 39.07 |
| | | J + 3 | 10-15 | 12.27 | 35.43 |
| Endoxan | 4 mg | J + 3 | 15-21 | 18.6 | 105.30 |

TABLE VII

| Compound tested | Injection | Quantity | Range of death | MTS | ILS % |
|---|---|---|---|---|---|
| Control $10^5$ cells | | | 10-11 | | |
| Compound of example 7 | J + 3 | 0.2 mg/mouse | 13-16 | 14.18 | 36.35 |
| ON COVIN | " | 0.5 µg/mouse | 10-13 | 10.8 | 3.85 |

TABLE VIII

| Number of L 1210 cells injected on day J | Compound used | Quantity* injected in mg/mouse | MTS | ILS % | Number of surviving mice |
|---|---|---|---|---|---|
| $10^3$ | Controls | — | 13 | | |
| | Example 8 | 0.1 mg/mouse | 16.4 | 50.5 | 3 |
| | Example 8 | 0.05 mg/mouse | 14.7 | 34.9 | 1 |
| | Example 7 | 0.2 mg/mouse | 16.3 | 25.4 | 7 |
| | Example 7 | 0.1 mg/mouse | 15 | 15.4 | 4 |
| $10^4$ | Controls | — | 10.9 | — | — |
| | Example 7 | 0.1 mg/mouse | 18 | 65.1 | 1 |
| | Example 8 | 0.1 mg/mouse | 13.7 | 25.7 | 3 |
| | Example 8 | 0.05 mg/mouse | 14.7 | 34.9 | 1 |
| $10^5$ | Controls | | 9.05 | | |
| | Example 8 | 0.1 mg/mouse | 13.8 | 52.5 | |
| | | 0.05 mg/mouse | 11.6 | 28.1 | |

*dose in mg/mouse × 50 = dose in mg/kg

TABLE IX

| Number of L 1210 cells injected on day J | | Quantity of the compound of example 7 used in mg/mouse | Injection | MTS | ILS % | Surviving mice |
|---|---|---|---|---|---|---|
| $10^4$ | Controls | | | 11.9 | | |
| | | 0.2 mg/mouse | single at J + 3 | 14.2 | 19.32 | 1 |
| | | 4 × (0.05 mg/mouse) | J + 3, fractionated at J + 3 + 4 + 5 + 6 | 14.4 | 21 | 0 |
| $10^5$ | Controls | | | 10.4 | | |
| | | 0.2 mg/mouse | single at J + 3, fraction- | 14.18 | 36.35 | |
| | | 4 × (0.05 mg/mouse) | | 13.4 | 28.85 | |

TABLE IX-continued

| Number of L 1210 cells injected on day J | Quantity of the compound of example 7 used in mg/mouse | Injection | MTS | ILS % | Surviving mice |
|---|---|---|---|---|---|
| | | ated at J + 3 + 4 + 5 + 6 | | | |

What is claimed is:

1. A dipyrido [4,3-b] [3,4-f] indole of the formula

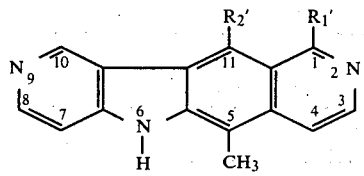

in which: R'₁ is hydrogen, hydroxy, lower alkyl, halogen or an amino group of the formula

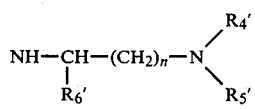

wherein
n is an integer from 1 to 3,
R'₆ is hydrogen or lower alkyl,
R'₄ and R'₅ each independently is hydrogen or lower alkyl, and
R'₂ is hydrogen or lower alkyl,
or a pharmaceutically acceptable salt thereof.

2. A compound according to claim 1, wherein R'₂ is methyl and R'₁ is hydrogen or hydroxy.

3. A compound according to claim 1, wherein R'₂ is hydrogen and R'₁ is chloro.

4. A compound according to claim 1, wherein R'₂ is methyl and R'₁ is halogen or an amino group of the formula

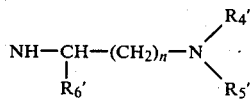

5. A compound according to claim 1, wherein R'₂ is hydrogen, and R'₁ is hydroxy, halogen or an amino group of the formula

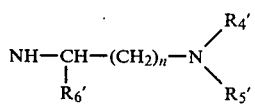

6. A compound according to claim 5, wherein R'₆ is hydrogen or methyl and R'₄ and R'₅ each independently is hydrogen methyl or ethyl.

7. A compound according to claim 1, selected from the group consisting of
5,11-dimethyl dipyrido [4,3-b] [;3,4-f] indole;
2,5,9,11-tetramethyl dipyrido [4,3-b] [3,4-f] indolinium diacetate;
5,11-dimethyl dipyrido [4,3-b] [3,4-f]indole acetate;
5,11-dimethyl dipyrido [4,3-b] [3,4-f] indole dihydrochloride;
1,2-dihydro-oxo-5-methyl dipyrido [4,3-b] [3,4-f] indole;
1-chloro-5-methyl dipyrido [4,3-b] [3,4-f] indole;
1[(γ-diethylaminopropyl) amino]5-methyl dipyrido [4,3-b 3,4-f] indole;
1-[(γ-dimethylaminopropyl) amino]5-methyl dipyrido [4,3-b ] [3,4-f] indole;
1[(β-dimethylaminoethyl) amino]-5-methyl dipyrido [4,3-b] [3,4] indole;
-1[(α-methyl-δ-diethylamino-butyl) amino]-5-methyl dipyrido [4,3-b] [3,4-f] indole;
-1-[(γ-amino-propyl)amino]-5-methyl dipyrido [4,3-b] [3,4-f] indole; and
1,2-dihydro-1-oxo-5,11-dimethyl dipyrido [4,3-b] [3,4-f] indole.

8. A process for preparing a compound according to claim 1, comprising the steps of:
(1) reacting a 6-amino-isoquinoline with 3-nitro-4-chloropyridine to form the corresponding 6-[4'-(3'-nitropyridyl) amino] isoquinoline;
(2) hydrogenating said isoquinoline thus obtained into the corresponding amino compound;
(3) reacting the corresponding amino compound with sodium nitrite to form the corresponding triazolopyridine;
(4) converting the triazolopyridine thus obtained into the corresponding dipyrido [4,3-b] [3,4-f] indole, and
(5) optionally forming the pharmaceutically acceptable salt of the dipyrido indole thus obtained.

9. A process according to claim 8, wherein the hydrogenation of step (2) is effected in the presence of a hydrogenation catalyst.

10. A process according to claim 8, wherein step (4) is effected in the presence of an inert high melting material.

11. A process according to claim 8, wherein the 6-amino-isoquinoline is one of the tautomers

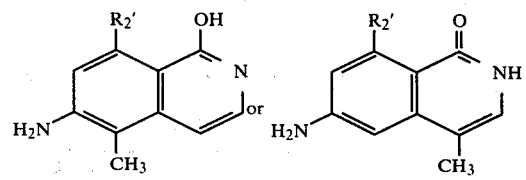

and is obtained by converting the amino group of a 2-methyl-3-amino-benzonitrile into an acetylamino group, converting the cyano group of the 2-methyl-3-acetylamino-benzonitrile into the aldehyde group, condensing the latter with malonic acid to form an acid of the formula

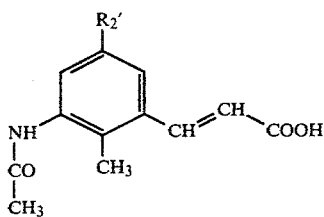

forming the azide of the acid cyclizing to form the corresponding isoquinolone, and eliminating the acetyl group from the amino group.

12. A process according to claim 8, wherein the 6-amino- isoquinoline is one of the tautomers

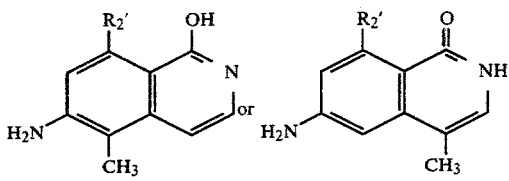

and is obtained by converting a 2-methyl-3-nitro-aniline into a (2-methyl-3-nitro-phenyl) chloropropionic acid, converting the latter compound into a 2-methyl-3-nitro-cinnamic acid by elimination of HCl, converting the nitro group into the amino group and thenthe acetylamino group, cyclizing to form the corresponding isoquinolone, and eliminating the acetyl group from the amino group.

13. A process according to claim 8, wherein the 6-aminoisoquinoline is one of the tautomers

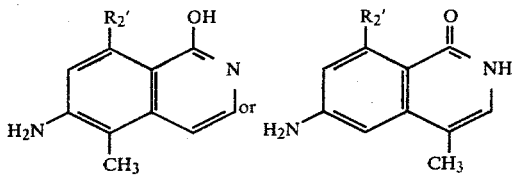

and is obtained by converting the chloromethyl group of

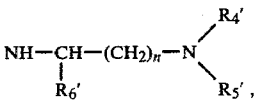

into an aldehyde group, condensing this aldehyde group with malonic acid to form the corresponding cinnamic acid, reducing the nitro group into an amino group, coverting the amino group into an acetylamino group, cyclizing to form the corresponding isoquinolone, and eliminating the acetyl group from the amino group.

14. A process according to claim 8, wherein $R,^1$ is $$NH-\underset{R_6'}{\underset{|}{CH}}-(CH_2)_n-N\underset{R_5'}{\overset{R_4'}{\diagdown}},$$

comprising the further steps of chlorinating the 1,2-dihydro-1-oxo- 5-methyl-dipyrido [4,3-b] [3,4-f] indole, and reacting the chlorinated compound so obtained with the appropriate amine.

15. A compound according to claim 1, wherein $R'_2$ is hydrogen.

16. A compound according to claim 1, wherein $R'_2$ is methyl.

* * * * *